United States Patent
Chandran et al.

(10) Patent No.: US 9,422,234 B2
(45) Date of Patent: Aug. 23, 2016

(54) PROSTATE SPECIFIC MEMBRANE ANTIGEN (PSMA) TARGETED NANOPARTICLES FOR THERAPY OF PROSTATE CANCER

(75) Inventors: Sachin S. Chandran, Highland Park, NJ (US); Sangeeta Ray, Ellicott City, MD (US); Martin G. Pomper, Baltimore, MD (US); Samuel R. Denmeade, Ellicott City, MD (US); Ronnie C. Mease, Fairfax, VA (US)

(73) Assignee: The Johns Hopkins University, Baltimore, MD (US)

( * ) Notice: Subject to any disclaimer, the term of this patent is extended or adjusted under 35 U.S.C. 154(b) by 664 days.

(21) Appl. No.: 12/744,982

(22) PCT Filed: Nov. 26, 2008

(86) PCT No.: PCT/US2008/013158
§ 371 (c)(1),
(2), (4) Date: Mar. 25, 2011

(87) PCT Pub. No.: WO2009/070302
PCT Pub. Date: Jun. 4, 2009

(65) Prior Publication Data
US 2011/0200677 A1     Aug. 18, 2011

Related U.S. Application Data

(60) Provisional application No. 61/004,791, filed on Nov. 30, 2007.

(51) Int. Cl.
*A61K 9/14* (2006.01)
*A61K 9/51* (2006.01)
*C07C 275/16* (2006.01)

(52) U.S. Cl.
CPC ............... *C07C 275/16* (2013.01); *A61K 9/51* (2013.01); *Y10S 977/773* (2013.01); *Y10S 977/906* (2013.01); *Y10S 977/911* (2013.01)

(58) Field of Classification Search
None
See application file for complete search history.

(56) References Cited

U.S. PATENT DOCUMENTS

| | | | |
|---|---|---|---|
| 2005/0158323 A1* | 7/2005 | Evans et al. | 424/155.1 |
| 2006/0251710 A1* | 11/2006 | Kwon et al. | 424/450 |
| 2009/0061010 A1* | 3/2009 | Zale | A61K 9/5153 424/501 |

FOREIGN PATENT DOCUMENTS

WO      2006/093991 A1    9/2006
WO      WO 2006093991 A1 *  9/2006

OTHER PUBLICATIONS

OC Farokhzad, S Jon, A Khademhosseini, TNT Tran, DA LaVan, R Langer. "Nanoparticle-Aptamer Bioconjugates: A New Approach for Targeting Prostate Cancer Cells." Cancer Research, vol. 64, Nov. 1, 2004, pp. 7668-7672.*

Farokhzad et al., "Nanoparticle-Aptamer Bioconjugates: A New Approach for Targeting Prostate Cancer Cells." Cancer Research (2004) vol. 64, pp. 7668-7672.

* cited by examiner

*Primary Examiner* — Isaac Shomer
(74) *Attorney, Agent, or Firm* — Mintz Levin Cohn Ferris Glovsky and Popeo, P.C.; Peter F. Corless; Richard B. Emmons

(57) ABSTRACT

The invention provides a nanoparticle composition that is decorated with a urea-based small-molecule peptidomimetic inhibitor of prostate specific membrane antigen (PSMA), which is expressed by almost all solid tumors. This strategy takes advantage of both the avidity of the functionalized nanoparticle for binding to PSMA and the ability of the nanoparticle to be retained for longer periods of time in the tumor due to enhanced leakage via EPR into the tumor interstitium and poor clearance due to underdeveloped or non-existent lymphatics within the tumor.

26 Claims, 5 Drawing Sheets

PROSTATE SPECIFIC MEMBRANE ANTIGEN (PSMA) TARGETED NANOPARTICLES FOR THERAPY OF PROSTATE CANCER

RELATED APPLICATIONS

This application is a 35 U.S.C. §371 U.S. national entry of International Application PCT/US2008/013158 (WO 2009/070302) having an International filing date of Nov. 26, 2008 which claims the benefit of U.S. Provisional Application Ser. No. 61/004,791, filed Nov. 30, 2007, the teachings of both of which are incorporated herein by reference in their entirety.

BACKGROUND OF THE INVENTION

1. Field of the Invention

The present invention provides novel nanoparticle compositions comprising a PSMA inhibitor, linker, nanoparticle and biologically active compound. The compositions of the invention are useful for providing methods of treating disorders, including cancer.

2. Background

Prostate cancer is the most commonly diagnosed non-cutaneous malignancy in American men and remains uniformly fatal once it undergoes metastasis (Jemal, A., et al. Cancer statistics, 2006. Ca-a Cancer Journal for Clinicians, 56: 106-130, 2006). Androgen ablation therapy is effective palliative therapy, but in all men tumor progression eventually occurs even when completely androgen-deprived (e.g. inhibition of both testicular and adrenal androgens) (Crawford, E. D., et al. N Engl J Med, 321: 419-424, 1989). Traditionally, prostate cancer was thought to be relatively resistant to cytotoxic chemotherapies administered following androgen ablation (Yagoda, A. and Petrylak, D. Cancer, 71: 1098-1109, 1993). However, two recent studies demonstrated a modest survival benefit in men with hormone refractory metastatic disease treated with docetaxel (Petrylak, D. P., et al. N Engl J Med, 351: 1513-1520, 2004; Tannock, I. F., et al. N Engl J Med, 351: 1502-1512, 2004). As with other cytotoxic therapies, docetaxel is associated with systemic toxicity that limits both the total dose and duration of therapy that can be administered (Petrylak, D. P., et al. N Engl J Med, 351: 1513-1520, 2004; Tannock, I. F., et al. N Engl J Med, 351: 1502-1512, 2004). To improve the therapeutic window, a number of approaches have been explored to target cytotoxic agents like docetaxel selectively to tumor with the goal of higher tumor concentration and lessening of toxicity to normal tissues. In this regard, various prostate tissue specific surface proteins have been evaluated as potential binding targets to improve tumor uptake and retention of therapeutic agents.

The most extensively characterized surface protein has been prostate-specific membrane antigen (PSMA). PSMA is highly expressed by prostate cancer compared to most normal tissue (Wright, G. L., et al. Urol Oncol, 1: 18-28, 1995; Israeli, R. S., et al. Cancer Res, 54: 1807-1811, 1994; Chang, S. S., et al. Cancer Res, 59: 3192-3198, 1909; Silver, D. A., et al. Clin Cancer Res, 3: 81-85, 199. PSMA expression has also been demonstrated to increase following androgen ablation (Montgomery, B. T., et al. Prostate, 21: 63-73, 1992; Wright, G. L., et al. Urology, 48: 326-334, 1996). Multiple studies have documented that PSMA is also expressed in the neovasculature of most solid tumors, but not in the vasculature of normal tissues (Israeli, R. S., et al. Cancer Res, 54: 1807-1811, 1994; Chang, S. S., et al. Cancer Res, 59: 3192-3198, 1999). PSMA is a carboxypeptidase and is relatively unique in its ability to function as both an N-acetylated alpha-linked dipeptidase and a gamma glutamyl (i.e. folate) hydrolase (Carter, R. E., et al. Proc Natl Acad Sci USA, 93: 749-753, 1996; Pinto, J. T., et al. Clin Cancer Res, 2: 1445-1451, 1996). Therefore, PSMA has been an attractive target for both targeted drug delivery and imaging. PSMA targeting approaches include the use of PSMA peptide substrates (Mhaka, A., et al. Cancer Biol Ther, 3: 551-558, 2004), PSMA-binding peptides (Aggarwal, S., et al. Cancer Res, 66: 9171-9177, 2006; Lupold, S. E. and Rodriguez, R. Mol Cancer Ther, 3: 597-603, 2004), RNA aptamers (Farokhzad, O. C., et al. Proc Natl Acad Sci USA, 103: 6315-6320, 2006; Lupold, S. E., et al. Cancer Res, 62: 4029-4033, 2002) or anti-PSMA monoclonal antibody-cytotoxin conjugates (Nanus, D. M., et al. J Urol, 170: S84-88; discussion S88-89, 2003). Efforts have also been made to image PSMA-positive prostate tumors using labeled small-molecule peptidomimetic PSMA inhibitors (Foss, C. A., et al. Clin Cancer Res, 11: 4022-4028, 2005; Zhou, J., et al. Nat Rev Drug Discov, 4: 1015-1026, 2005) and monoclonal antibodies (Bander, N. H. Nat Clin Pract Urol, 3: 216-225, 2006; Lopes, A. D., et al. Cancer Res, 50: 6423-6429, 1990).

Previously Zhou et al reviewed a series of urea-based PSMA inhibitors with high picomolar to low nanomolar $K_i$ values (Zhou, J., et al. Nat Rev Drug Discov, 4: 1015-1026, 2005). Radiolabeled versions of these inhibitors have been used to selectively image PSMA-expressing prostate cancer xenografts (Foss, C. A., et al. Clin Cancer Res, 11: 4022-4028, 2005). On the basis of these studies, we developed an approach to functionalize nanoparticles with a highly potent urea-based PSMA inhibitor which could enable homing of the nanoparticle to prostate cancer. The small-molecule inhibitor would allow for the generation of a highly decorated nanoparticle surface in which multiple ligand-protein binding interactions would produce an avidity effect that would enhance the binding of the nanoparticle to PSMA.

In a previous study, it was demonstrated that docetaxel could be readily encapsulated into poly(lactide-β-ethylene glycol-(β-lactide) (PLA-PEG-PLA) nanoparticles and that these nanoparticles exhibited in vivo efficacy (Chandran, S. S., Gerber, S. A., Rosen, M., and Denmeade, S. R. Formulation, in vitro efficacy and in vivo pharmacokinetics of polymeric nanoparticles bearing the natural toxin thapsigargin and its analog 12ADT. Manuscript in preparation). PLA-PEG-PLA was chosen as the controlled release system because its component polymers have been previously demonstrated to be biocompatible and have been extensively used in drug development (Greenwald, R. B., et al. Adv Drug Deliv Rev, 55: 217-250, 2003; Lee, J. S., et al. Eur J Pharm Biopharm, 59: 169-175, 2005; Li, S. and McCarthy, S. Biomaterials, 20: 35-44, 1999; Shive, M. S. and Anderson, J. M. Adv Drug Deliv Rev, 28: 5-24, 1997).

What is desired is to provide novel nanoparticle compositions comprising a biologically active material and PSMA inhibitors which are attached to the nanoparticle via a linker, while retaining high affinity to PSMA.

SUMMARY OF THE INVENTION

In one aspect, the invention provides a nanoparticle composition comprising, a) a prostate specific membrane antigen (PSMA) inhibitor; b) a linker, c) a biologically active agent; and d) a nanoparticle.

In another aspect, the invention provides a method for treating or preventing a disease or disorder in a subject, the method comprising the step of administering to the subject a nanoparticle composition, such that the administration of the nanoparticle composition is effective to treat or prevent said disease or disorder, wherein the nanoparticle composition comprises a) a prostate specific membrane antigen (PSMA) inhibitor; b) a linker, c) a biologically active agent; and d) a nanoparticle; or a nanoparticle composition of formula I:

wherein
X is an organic small molecule PSMA inhibitor;
Y is an organic linker;
Z is a nanoparticle comprising a biologically active agent;
m is 1-1000 and
n is 1-1000.

DETAILED DESCRIPTION OF THE INVENTION

Definitions

Figure 1:
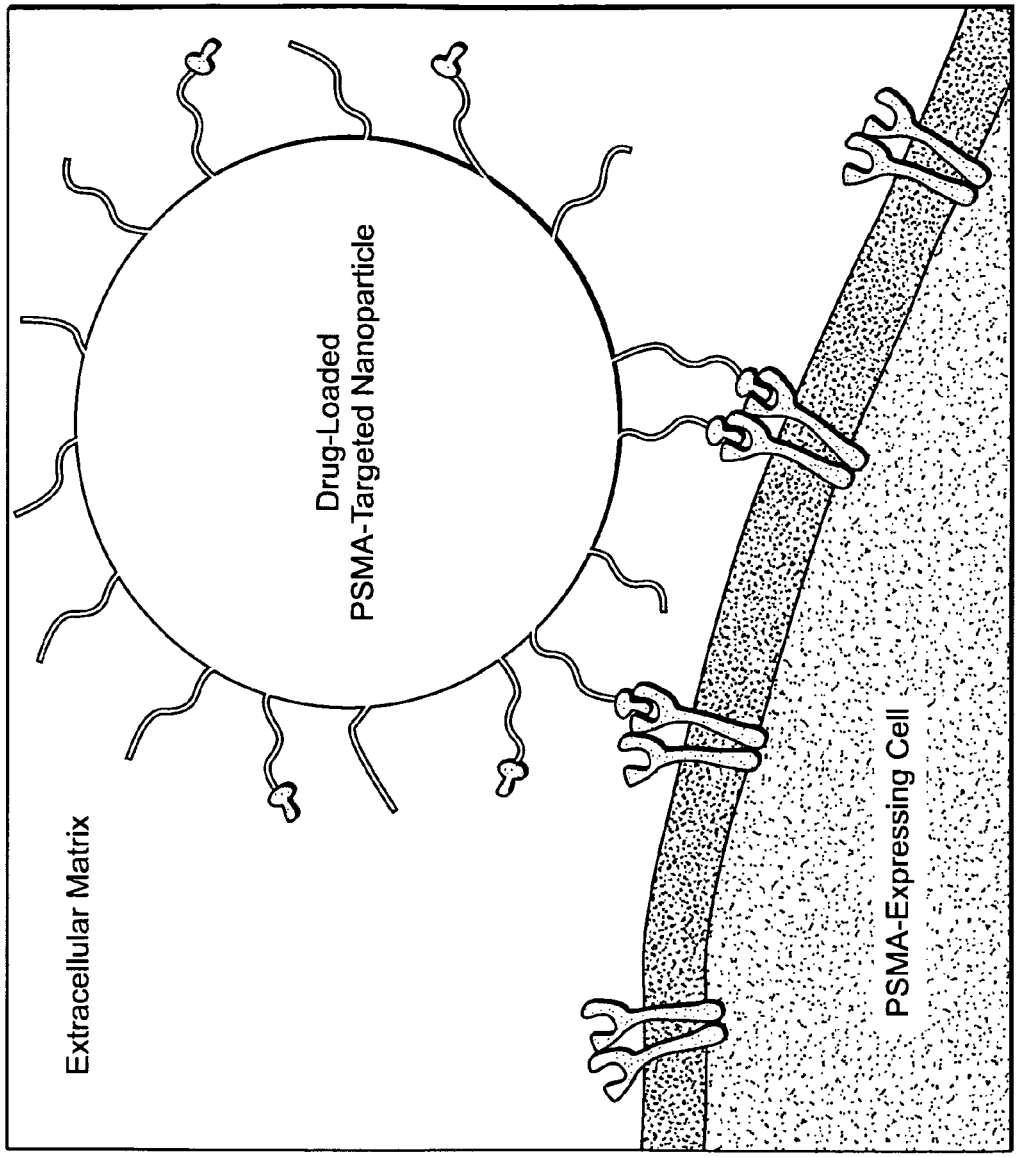
FIG. 1: A general schematic demonstrating the binding of the nanoparticle. PSMA in dimeric form is observed on the cell surface. The polymeric nanoparticle has multiple PEG arms, some of which have the PSMA inhibitor attached to it. Total surface coverage by the inhibitor was computed to be $2.23 \times 10^{17}$ molecules/m$^2$ of surface area of the nanoparticles (~30,000 inhibitor molecules/nanoparticle).
Figure 1:
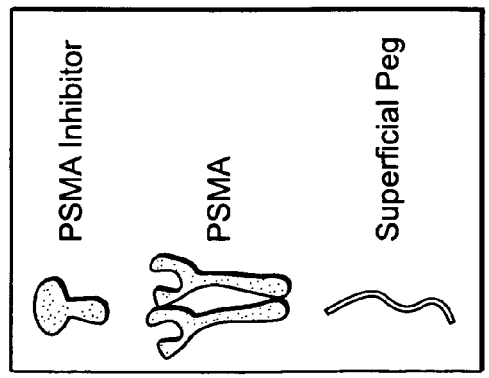

As used herein a "nanoparticle" is a particle of submicron dimensions. Optionally, the nanoparticle is comprised of polymeric materials and may be comprised of natural or synthetic polymeric materials. As used herein, "synthetic polymeric materials" do not include natural polymers, such as proteins or starch. Examples of suitable polymeric materials include, but are not limited to homopolymers, copolymers, random polymers, graft polymers, alternating polymers, block polymers, branch polymers, arborescent polymers and dendritic polymers. Nanoparticles include nanospheres, which are nanoparticles having a substantially round, spherical or globular structure. Nanoparticles of the present invention may be used to carry therapeutic agents for delivery to target cells or tissue. As used herein, carrying of a therapeutic agent by a nanoparticle includes encapsulation of the therapeutic agent by the nanoparticle, or attachment, adsorbtion or other association of the therapeutic agent to or with the nanoparticle. Suitably, nanoparticles may be biodegradable, for example being made of FDA-approved polymers and reagents for internal use. Nanoparticles may optionally comprise surface ligands that enhance their transfer to target cells.

Suitably, nanoparticles may be at least 20 nm, at least 25 nm, at least 35 nm, at least 50 nm or at least 75 nm in average diameter. Suitably, nanoparticles may be less than 600 nm, less than 500 nm, less than 300 nm, less than 250 nm, less than 200 nm, less than 150 nm or less than 100 nm in average diameter. Suitably, nanoparticles are of a size that does not induce an inflammatory response in the target cell.

As used herein, a "therapeutic agent" is an agent, or combination of agents, that treats a cell, tissue or subject having a condition requiring therapy, when contacted with the cell, tissue or subject. The therapeutic agent may be suitably encapsulated, adsorbed or attached to the nanoparticle. Non-limiting examples of suitable therapeutic agents include small molecules, drugs, polypeptides, antagomirs, cytotoxic agents, chemotherapeutic agents, anti-angiogenic agents, radioactive agents, imaging agents, cytokines, growth factors, apoptotic pathway effectors, agonists or antagonists, antibodies, radionuclides, anti-inflammatory agents, analgesics or polynucleotide sequences, or other agents disclosed herein.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are C$_{1-12}$ alkyl groups. Especially preferred alkyl groups are methyl, ethyl, propyl, butyl, and 3-pentyl.

"Alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 12 carbon atoms.

"Alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 12 carbon atoms.

As used herein, the term "aryl" includes groups that contain 1 to 3 separate or fused rings and from 6 to about 18 ring atoms, without hetero atoms as ring members. Specifically preferred carbocyclic aryl groups include phenyl, and naphthyl including 1-napthyl and 2-naphthyl.

The term "aralkyl" or "arylalkyl" refers to an alkyl residue attached to an aryl ring. Examples of aralkyl include, but are not limited to, benzyl, phenethyl and the like. The term "heteroaralkyl" or "heteroarylalkyl" refers to an alkyl residue attached to a heteroaryl ring. Examples include, but are not limited to, pyridinylmethyl, pyrimidinylethyl and the like.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups will have 1 to about 2 carbon atoms.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 12 carbon atoms.

"Haloalkoxy" represents a haloalkyl group as defined above with the indicated number of carbon atoms attached through an oxygen bridge.

As used herein, the term "alkylthio" includes those groups having one or more thioether linkages and preferably from 1 to about 12 carbon atoms.

As used herein, the term "alkylsulfinyl" includes those groups having one or more sulfoxide (SO) linkage groups and typically from 1 to about 12 carbon atoms.

As used herein, the term "alkylsulfonyl" includes those groups having one or more sulfonyl ($SO_2$) linkage groups and typically from 1 to about 12 carbon atoms.

As used herein, the term "alkylamino" includes those groups having one or more primary, secondary and/or tertiary amine groups and typically from 1 to about 12 carbon atoms.

"Halo," "hal," or "halogen" as used herein refers to fluoro, chloro, bromo, or iodo; and "counter-ion" is used to represent a small, negatively charged species such as chloride, bromide, hydroxide, acetate, sulfate, and the like.

As used herein, "cycloalkyl" or "carbocyclic" group are used interchangeably and are intended to mean any stable 3- to 7-membered monocyclic or bicyclic or 7- to 13-membered bicyclic or tricyclic group, any of which may be saturated or partially unsaturated. In addition to those exemplified elsewhere herein, examples of such carbocycles include, but are not limited to, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, and tetrahydronaphthyl.

As used herein, the term "heterocyclic" or "heterocycloalkyl" is intended to include saturated, or partially unsaturated groups having 1 to 3 (preferably fused) rings with 3 to about 8 members per ring at least one ring containing an atom selected from N, O or S. The nitrogen and sulfur heteroatoms may optionally be oxidized.

As used herein, the term "heteroaryl" is intended to include cyclic unsaturated (aromatic) groups having 1 to 3 (preferably fused) rings with 3 to about 8 members per ring at least one ring containing an atom selected from N, O or S. The nitrogen and sulfur heteroatoms may optionally be oxidized.

Examples of heterocyclic and heteroaryl groups include, but are not limited to, those exemplified elsewhere herein and further include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazolyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocyclic and heteroaryl groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl. Also included are fused ring and Spiro compounds containing, for example, the above heterocycles.

In certain instances, any of the groups described above may be bonded to two separate groups, e.g., an alkyl group includes alkenylene groups, e.g., —$CH_2$—, —$CH_2CH_2$—, and the like.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -dihetero arylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

It is understood that the aryls, heteroaryls, alkyls, and the like can be further substituted. In accordance with the invention, any of the aryls, substituted aryls, heteroaryls and substituted heteroaryls described herein, can be any aromatic group. Aromatic groups can be substituted or unsubstituted.

A "pharmaceutically acceptable carrier" refers to a biocompatible solution, having due regard to sterility, pH, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)$n-COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

Compositions of the Invention

In one aspect, the invention provides a nanoparticle composition comprising, a) a prostate specific membrane antigen (PSMA) inhibitor; b) a linker, c) a biologically active agent; and d) a nanoparticle.

In one embodiment, the invention provides a nanoparticle composition wherein the PSMA inhibitor is attached to a linker.

In another embodiment, the invention provides a nanoparticle composition wherein the biologically active agent is encapsulated in the nanoparticle.

In certain embodiments, the invention provides a nanoparticle composition wherein the linker is attached to the nanoparticle.

In one embodiment, the invention provides a nanoparticle composition of formula I:

wherein
X is an organic small molecule PSMA inhibitor;
Y is an organic linker;
Z is a nanoparticle comprising a biologically active agent;
m is 1-1000 and
n is 1-1000.

In certain embodiments, X is a compound of formula II,

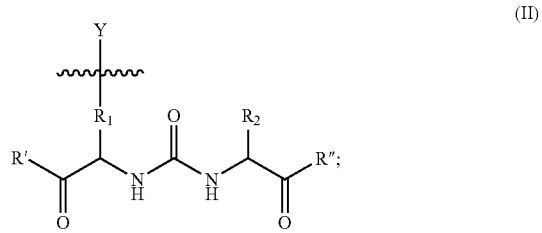

wherein,
$R_1$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

$R_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, or optionally substituted carbocyclic;

R' and R" are each independently —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O—R$_4$, —C(O)R$_4$, —C(O)NR$_3$R$_4$, or —N(R$_3$)C(O)R$_4$;

R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

or a pharmaceutically acceptable salt thereof.

In other embodiments, R' and R" are each independently —OR$_4$.

In another embodiment, each R$_4$ is independently H, methyl, or ethyl.

In certain embodiments, R$_1$ is a side chain of a naturally occurring amino acid.

In other embodiments, R$_1$ is optionally substituted alkyl, containing 0, 1, 2, or 3 heteroatoms selected from O, S, or N; optionally substituted arylalkyl, optionally substituted alkoxy, or optionally substituted heterocyclic.

In a further embodiment, R$_1$ is (CH$_2$)$_p$—O—Y, (CH$_2$)$_p$—S—Y, (CH$_2$)$_p$—SO—Y, (CH$_2$)$_p$—SO$_2$—Y, (CH$_2$)$_p$—N(R$_3$)S(O)$_2$—Y, (CH$_2$)$_p$—N(R$_3$)(SO$_2$)NR$_3$—Y, (CH$_2$)$_p$—NR$_3$—Y, (CH$_2$)$_p$—C(O)—O—Y, (CH$_2$)$_p$—C(O)—Y, (CH$_2$)$_p$—C(O)NR$_3$—Y, or (CH$_2$)$_p$—N(R$_3$)C(O)—Y;

R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 1-6.

In still a further embodiment, R$_1$ is (CH$_2$)$_p$—O—Y, (CH$_2$)$_p$—NR$_3$—Y, (CH$_2$)$_p$—C(O)—O—Y, (CH$_2$)$_p$—C(O)—Y, (CH$_2$)$_p$—C(O)NR$_3$—Y, or (CH$_2$)$_p$—N(R$_3$)C(O)—Y;

R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 3-6.

In a further embodiment, R$_1$ is (CH$_2$)$_p$—NR$_3$—Y.

In another embodiment, R$_2$ is optionally substituted alkyl, containing 0, 1, 2, or 3 heteroatoms selected from O, S, or N; or optionally substituted arylalkyl.

In certain embodiments, R$_2$ is a side chain of a naturally occurring amino acid.

In a further embodiment, R$_2$ is (CH$_2$)$_p$—OR$_4$, (CH$_2$)$_p$—SR$_4$, (CH$_2$)$_p$—SOR$_4$, (CH$_2$)$_p$—SO$_2$R$_4$, (CH$_2$)$_p$—N(R$_3$)S(O)$_2$—R$_4$, (CH$_2$)$_p$—N(R$_3$)(SO$_2$)NR$_3$R$_4$, (CH$_2$)$_p$—NR$_3$R$_4$, (CH$_2$)$_p$—C(O)—O—R$_4$, (CH$_2$)$_p$—C(O)R$_4$, (CH$_2$)$_p$—C(O)NR$_3$R$_4$, or (CH$_2$)$_p$—N(R$_3$)C(O)R$_4$;

R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 1-6.

In a further embodiment, R$_2$ is (CH$_2$)$_p$—OR$_4$, (CH$_2$)$_p$—C(O)—O—R$_4$, (CH$_2$)$_p$—C(O)R$_4$, (CH$_2$)$_p$—C(O)NR$_3$R$_4$, or (CH$_2$)$_p$—N(R$_3$)C(O)R$_4$;

R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 1-3.

In a further embodiment, R$_2$ is (CH$_2$)$_p$—C(O)—O—R$_4$.

In certain embodiments, Y is

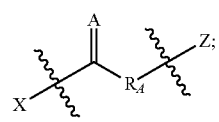

wherein

A is O, S, NH, N(alkyl) or N(aryl); and

R$_A$ is optionally substituted alkyl, optionally substituted alkenyl or optionally substituted alkynyl, each containing heteroatoms selected from O, S, or N.

In one embodiment, A is C═O.

In another embodiment, R$_A$ is (CH$_2$)$_r$-Q-Z, (CH$_2$O)$_r$-Q-Z, (CH$_2$NH)$_r$-Q-Z, (CH$_2$NR$_B$)$_r$-Q-Z, or combinations thereof, wherein Q is CO, C(O)O, C(O)NH, C(O)NR$_B$, OCO, OC(O)O, OC(O)NH, OC(O)NR$_B$, NHCO, NHC(O)O, NHC(O)NH, NHC(O)NR$_B$, NR$_B$CO, NR$_B$C(O)O, NR$_B$C(O)NH, NR$_B$C(O)NR$_B$, CS, C(S)O, C(S)NH, C(S)NR$_B$, OCS, OC(S)O, OC(S)NH, OC(S)NR$_B$, NHCS, NHC(S)O, NHC(S)NH, NHC(S)NR$_B$, NR$_B$CS, NR$_B$C(S)O, NR$_B$C(S)NH, NR$_B$C(S)NR$_B$;

each R$_B$ is independently optionally substituted alkyl or optionally substituted aryl; and r is 3-20.

In a further embodiment, Q is C(O)O, NHC(S)NH, or NHC(O)NH.

In one embodiment, Z is a nanoparticle comprising Poly-lactide-b-ethylene glycol-b-lactide (PLA-PEG-PLA), polylactide (PLA), polyglycolide, polylactide-polyglycolide, poly(lactide-co-glycolide), polyethylene glycol-co-lactide (PEG-PLA), poly(lactic-co-glycolic acid), polyhydroxybutyric acid, polyhydroxyvaleric acid, polycaprolactone, polyesteramide, polycyanoacrylate, poly(amino acids), polycarbonate, polyanhydride, poly alkylcyanoacrylate, polyethylene glycol (PEG), polysialic acid, polylactic (polylactide), polyglycolic acid (polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose, methoxypolyethylene glycol, avidin, biotin, or combinations thereof.

In a further embodiment, Z is a nanoparticle comprising Poly-lactide-b-ethylene glycol-b-lactide (PLA-PEG-PLA), polylactide (PLA), polyglycolide, polylactide-polyglycolide, poly(lactide-co-glycolide), polyethylene glycol-co-lactide (PEG-PLA), or combinations thereof.

In another embodiment, Z comprises one or more polymers, wherein the one or more polymers have an average molecular weight from about 2,000 Da to about 5,000 Da.

In other embodiments, the nanoparticle has a diameter ranging from about 1 nm to about 500 nm. In certain embodiments, the diameter of the nanoparticle ranges from about 10 nm to about 250 nm; about 25 nm to about 200 nm; or about 10 nm to about 50 nm.

In another embodiment, the biologically active agent is selected from a nucleic acid, a polynucleotide, an amino acid, a peptide a protein, a polypeptide, a carbohydrate, a lipid, a glycoprotein, a glycan, a lipoprotein, and a small molecule.

In certain embodiments, the biologically active agent is a known pharmaceutical.

In a further embodiment, the biologically active agent is selected from an anti-AIDS agent, anti-cancer agent, antibiotic, antioxidants, immunosuppressant, anti-viral agent, enzyme inhibitor, protease inhibitor, reverse transcriptase inhibitor, fusion inhibitor, neurotoxin, opiod, hypnotic, antihistamine, lubricant, tranquilizer, anti-convulsant, muscle relaxant, anti-Parkinson agent, anti-spasmodic, muscle contractant, channel blocker, miotic, anti-cholinergic, anti-glaucoma agent, anti-parasite, anti-protozoal, modulator of cell-extracellular matrix interaction, cell growth inhibitor, anti-adhesion agent, vasodilating agent, inhibitor of DNA, inhibitor of RNA, inhibitor of protein synthesis, inhibitors of apoptotic genes, modulators of transcription factors, anti-hypertensive, analgesic, anti-pyretic, steroidal anti-inflammatory agent, non steroidal anti-inflammatory agent, anti-angiogenic, anti-secretory, anticoagulant, antithrombotic agent, local anesthetic, ophthalmic, prostaglandin, anti-depressant, anti-psychotic, anti-emetic, antiproliferative, anti-migration, antiangiogenic, antithrombotic, anti-inflammatory, antiphlogistic, cytostatic, cytotoxic, anticoagulative, antibacterial, antiviral and/or antimycotic agent and an imaging agent.

In a further embodiment, the biologically active agent is selected from actinomycin D, ametantrone, 9-Aminocamptothecin, aminoglutethimide, amsacrine, anastrozole, antagonists of purine and pyrimidine bases, anthracycline, aromatase inhibitors, asparaginase, antiestrogens, bendamustine, bexarotene, biolimus A9, bleomycin, buserelin, busulfan, calicheamicins, camptothecin, camptothecin derivatives, capecitabine, carboplatin, carmustine, chlorambucil, cisplatin, cladribine, cyclophosphamide, cytarabine, cytosine arabinoside, alkylating cytostatics, dacarbazine, dactinomycin, daunorubicin, 5'-deoxy-5-fluorouridine, docetaxel, doxorubicin (adriamycin), doxorubicin lipo, epirubicin, estramustine, etoposide, exemestane, fludarabine, fluorouracil, folic acid antagonists, formestane, gemcitabine, glucocorticoids, goserelin, hormones and hormone antagonists, hycamtin, hydroxyurea, idarubicin, ifosfamide, imatinib, irinotecan, letrozole, leuprorelin, lomustine, maytansinoids, melphalan, mercaptopurine, methotrexate, miltefosine, mitomycins, mitopodozide, antimitotic agents, mitoxantrone, nimustine, oxaliplatin, oxazaphosphorines, paclitaxel, pentostatin, podophyllotoxin derivatives, procarbazine, rapamycin, rhodomycin D, tamoxifen, temozolomide, teniposide, testolactone, thiotepa, thioguanine, topoisomerase inhibitors, topotecan, treosulfan, tretinoin, triptorelin, trofosfamides, vinca alkaloids, vinblastine, vincristine, vindesine, vinorelbine, cytostatically active antibiotics, chlorethamine, cyclophosphamide, trofosfamide, ifosfamide, melphalan, chlorambucil, busulfan, thiotepa, carmustine, lomustine, dacarbazine, procarbazine, temozolomide, treosulfan, estramustine, nimustine, daunorubicin, doxorubicin (adriamycin), dactinomycin, mitomycin C, bleomycin, epirubicin (4-epi-adriamycin), idarubicin, mitoxantrone, amsacrine, actinomycin D, methotrexate, 5-fluorouracil, 6-thioguanin, 6-mercaptopurine, fludarabine, cladribine, pentostatin, gemcitabine, cytarabine, azathioprine, raltitrexed, capecitabine, cytosine arabinoside, thioguanine, mercaptopurine, vincristine, vinblastine, vindesine, etoposide, alkaloids, podophyllotoxins, cisplatin, carboplatin, oxaliplatin, vincristine, vinblastine, vindesine, vinorelbine, Taxol®, etoposide, teniposide, camptothecin, topotecan, irinotecan, hydroxycarbamide (hydroxyurea), imatinib, Miltefosine®, amsacrine, topotecan (inhibitor of topoisomerase-I), pentostatin, bexarotene, biolimus A9, rapamycin (sirolimus), rhodomycin D, ametantrone, bendamustine, oxazaphosphorine, 5'-deoxy-5-fluorouridine, 9-aminocamptothecin, podophyllotoxin derivatives, mitopodozide, vinca alkaloids, calicheamicins, maytansinoids, tretinoin, asparaginase, trastuzumab (Herceptin®), alemtuzumab (MabCampath®) and rituximab (MabThera®), glucocorticoids, prednisone, estrogens, fosfestrol, estramustine, LHRH, buserelin, goserelin, leuprorelin, triptorelin, flutamide, cyproterone acetate, tamoxifen, toremifen, aminoglutethimide, formestane, exemestane, letrozole, anastrozole, Cu/Zn SOD, glutathione, anti-apoptotic polypeptides.

In certain embodiments, the biologically active agent is docetaxel.

In another embodiment, the invention provides a nanoparticle composition of formula III:

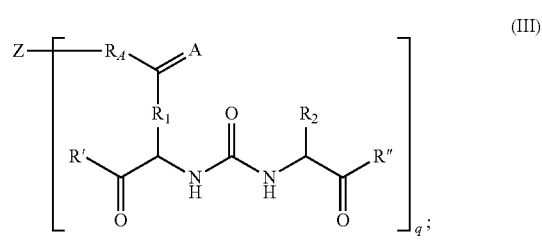

(III)

wherein, $R_1$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

$R_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, or optionally substituted carbocyclic;

R' and R" are each independently —$OR_4$, —$SR_4$, —$SOR_4$, —$SO_2R_4$, —$N(R_3)S(O)_2$—$R_4$, —$N(R_3)(SO_2)NR_3R_4$, —$NR_3R_4$, —$C(O)$—$O$—$R_4$, —$C(O)R_4$, —$C(O)NR_3R_4$, or —$N(R_3)C(O)R_4$;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

A is O, S, NH, N(alkyl) or N(aryl); and $R_A$ is optionally substituted alkyl, optionally substituted alkenyl or optionally substituted alkynyl, each containing heteroatoms selected from O, S, or N;

Z is a nanoparticle comprising a biologically active agent; and q is 1-1000;

or a pharmaceutically acceptable salt thereof.

In one embodiment, R' and R" are each independently —$OR_4$; and each $R_4$ is independently H, methyl, or ethyl.

In another embodiment, $R_1$ is optionally substituted alkyl, containing 0, 1, 2, or 3 heteroatoms selected from O, S, or N; optionally substituted arylalkyl, optionally substituted alkoxy, or optionally substituted heterocyclic.

In a further embodiment, $R_1$ is $(CH_2)_p$—O—, $(CH_2)_p$—$NR_3$—, $(CH_2)_p$—C(O)—O—, $(CH_2)_p$—C(O)—, $(CH_2)_p$—C(O)$NR_3$—, or $(CH_2)_p$—$N(R_3)C(O)$—;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 3-6.

In certain embodiments, $R_1$ is $(CH_2)_p$—$NR_3$—.

In one embodiment, $R_2$ is optionally substituted alkyl, containing 0, 1, 2, or 3 heteroatoms selected from O, S, or N; or optionally substituted arylalkyl.

In a further embodiment, $R_2$ is $(CH_2)_p$—$OR_4$, $(CH_2)_p$—C(O)—O—$R_4$, $(CH_2)_p$—$C(O)R_4$, $(CH_2)_p$—$C(O)NR_3R_4$, or $(CH_2)_p$—$N(R_3)C(O)R_4$;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic; and p is 1-3.

In a further embodiment, $R_2$ is $(CH_2)_p$—C(O)—O—$R_4$.

In certain embodiments, A is C=O; $R_A$ is $(CH_2)_r$-Q-, $(CH_2O)_r$-Q-, $(CH_2NH)_r$-Q-, $(CH_2NR_B)_r$-Q-, or combinations thereof, wherein Q is CO, C(O)O, C(O)NH, C(O)$NR_B$, OCO, OC(O)O, OC(O)NH, OC(O)$NR_B$, NHCO, NHC(O)O, NHC(O)NH, NHC(O)$NR_B$, $NR_B$CO, $NR_B$C(O)O, $NR_B$C(O)NH, $NR_B$C(O)$NR_B$, CS, C(S)O, C(S)NH, C(S)$NR_B$, OCS, OC(S)O, OC(S)NH, OC(S)$NR_B$, NHCS, NHC(S)O, NHC(S)NH, NHC(S)$NR_B$, $NR_B$CS, $NR_B$C(S)O, $NR_B$C(S)NH, $NR_B$C(S)$NR_B$;

each $R_B$ is independently optionally substituted alkyl or optionally substituted aryl; and r is 3-20.

In a further embodiment, Q is C(O)O, NHC(S)NH, or NHC(O)NH.

In certain embodiments, Z is a nanoparticle comprising Poly-lactide-b-ethylene glycol-b-lactide (PLA-PEG-PLA), polylactide (PLA), polyglycolide, polylactide-polyglycolide, poly(lactide-co-glycolide), polyethylene glycol-co-lactide (PEG-PLA), or combinations thereof.

In another embodiment, the invention provides a nanoparticle composition of formula IV:

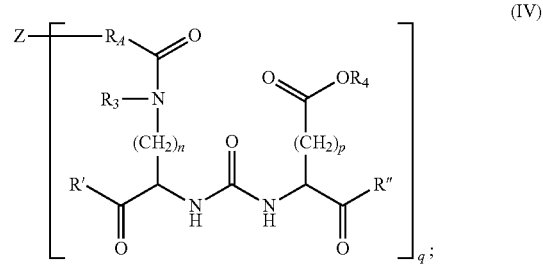

(IV)

wherein,

R' and R" are each independently —$OR_4$, —$SR_4$, —$SOR_4$, —$SO_2R_4$, —$N(R_3)S(O)_2$—$R_4$, —$N(R_3)(SO_2)NR_3R_4$, —$NR_3R_4$, —C(O)—O—$R_4$, —$C(O)R_4$, —$C(O)NR_3R_4$, or —$N(R_3)C(O)R_4$;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

$R_A$ is optionally substituted alkyl, optionally substituted alkenyl or optionally substituted alkynyl, each containing heteroatoms selected from O, S, or N;

Z is a nanoparticle comprising a biologically active agent; and q is 1-1000;

or a pharmaceutically acceptable salt thereof.

In one embodiment, R' and R" are each independently —$OR_4$; and each $R_4$ is independently H, methyl, or ethyl.

In another embodiment, $R_A$ is $(CH_2)_r$-Q-, $(CH_2O)_r$-Q-, $(CH_2NH)_r$-Q-, $(CH_2NR_B)_r$-Q-, or combinations thereof, wherein Q is CO, C(O)O, C(O)NH, C(O)$NR_B$, OCO, OC(O)O, OC(O)NH, OC(O)$NR_B$, NHCO, NHC(O)O, NHC(O)NH, NHC(O)$NR_B$, $NR_B$CO, $NR_B$C(O)O, $NR_B$C(O)NH, $NR_B$C(O)$NR_B$, CS, C(S)O, C(S)NH, C(S)$NR_B$, OCS, OC(S)O, OC(S)NH, OC(S)$NR_B$, NHCS, NHC(S)O, NHC(S)NH, NHC(S)$NR_B$, $NR_B$CS, $NR_B$C(S)O, $NR_B$C(S)NH, $NR_B$C(S)$NR_B$;

each $R_B$ is independently optionally substituted alkyl or optionally substituted aryl; and r is 3-20.

In a further embodiment, Q is C(O)O, NHC(S)NH, or NHC(O)NH.

In one embodiment, Z is a nanoparticle comprising Poly-lactide-b-ethylene glycol-b-lactide (PLA-PEG-PLA), polylactide (PLA), polyglycolide, polylactide-polyglycolide, poly(lactide-co-glycolide), polyethylene glycol-co-lactide (PEG-PLA), or combinations thereof.

The compounds and compositions herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Nanoparticles may be synthesized using any method described in the art, or disclosed herein. In one embodiment, nanoparticles are modified by polyethylene glycol (PEG) conjugation, a process known in the art as "PEGylation." In certain embodiments, nanoparticles may be suitably made using polygycolic acid (PGA) and/or poly-lactic acid (PLA) to form a polymer or copolymer used to construct the nanoparticle matrix. Nanoparticle uptake and transfection into specific cells is enhanced by complexing nanoparticles to ligands specific to PSMA. Additional methods of increasing exposure to PSMA includes changes to PEG surface density which may be optionally modified to uncover the hydrophobic and charged polymeric core, or PEG carrier hydrolysis to expose the hydrophobic core of the nanoparticle.

In one embodiment, a PEG arm was introduced as a spacer using an α-amino-co-hydroxy terminated poly(ethylene glycol-b-ε-caprolactone) (PEG-PCL) polymer chain in order to maintain sufficient distance between the small-molecule PSMA inhibitor and the nanoparticle surface. PEG functions in this targeting application to decrease nonspecific protein binding (i.e. 'bio-fouling') and minimizes particle clearance by the reticuloendothelial system. Additionally, the PEG-PCL would partition such that the PEG would orient towards the surface of the nanoparticle thus improving presentation of the attached binding ligand. Using this rationale, a strategy was developed to generate a PEGylated urea-based PSMA inhibitor incorporated into a PLA-PEG-PLA nanoparticle, as shown in FIG. 1. The components of this system and the PSMA inhibitor conjugated nanoparticles were then characterized for their ability to inhibit the enzymatic activity of PSMA. Subsequently, docetaxel encapsulated, PSMA-targeted nanoparticles were evaluated for their ability to bind to PSMA expressing human LNCaP prostate cancer cells and to selectively inhibit their growth in vitro.

Targeted therapy for cancer has gained considerable importance recently with various improvements not only in target identification, but also in small-molecule or antibody development. It has also been demonstrated that polymeric nanoparticles can passively target tumors via the enhanced permeability and retention (EPR) effect. Here, a combined approach is described in which the surface of a nanoparticle is decorated with a urea-based small-molecule peptidomimetic inhibitor of prostate specific membrane antigen (PSMA). This strategy takes advantage of both the avidity of the functionalized nanoparticle for binding to PSMA and the ability of the nanoparticle to be retained for longer periods of time in the tumor due to enhanced leakage via EPR into the tumor interstitium and poor clearance due to underdeveloped or non-existent lymphatics within the tumor. Previous baseline studies with non-functionalized poly(lactide-β-ethylene glycol-β-lactide) (PEG-PLA) nanoparticles loaded with docetaxel demonstrated tumor regression in human PC3 prostate tumor xenografts. As an initial step to introducing the targeting moiety, the amino terminus of the small-molecule PSMA inhibitor was conjugated to PEG ($M_n$ 3400) bearing an activated carboxyl group to obtain a PEGylated inhibitor. Studies undertaken using a radiolabeled PSMA-substrate based assay established that the PEGylated inhibitor had an $IC_{50}$ value similar to the uncomplexed inhibitor. Subsequently, nanoparticles loaded with docetaxel were formulated using a mixture of poly(lactide-β-ethylene glycol-β-lactide) and PSMA-inhibitor bound α-amino-ω-hydroxy terminated poly(ethylene glycol-β-ε-caprolactone). In vitro studies using these nanoparticles demonstrated selective cytotoxicity against PSMA-producing cells. Binding of fluorescently labeled PSMA-targeted particles to PSMA-producing cells has also been directly observed using fluorescence microscopy and observed in secondary fashion using a PSMA substrate based enzyme inhibition assay.

Methods of the Invention

In one aspect, the invention provides a method for treating or preventing a disease or disorder in a subject, the method comprising the step of administering to the subject a nanoparticle composition, such that the administration of the nanoparticle composition is effective to treat or prevent said disease or disorder, wherein the nanoparticle composition comprises a) a prostate specific membrane antigen (PSMA) inhibitor; b) a linker, c) a biologically active agent; and d) a nanoparticle; or a nanoparticle composition of formula I:

$$(X)_m\text{—}(Y)_n\text{—}Z \qquad (I);$$

wherein
X is an organic small molecule PSMA inhibitor;
Y is an organic linker;
Z is a nanoparticle comprising a biologically active agent;
m is 1-1000 and
n is 1-1000.

In one embodiment, the disease is cancer or a proliferation disease.

In a further embodiment, the disease is cancer, tumor or carcinoma.

In certain embodiments, the disease is prostate cancer, bladder cancer, bone cancer, brain cancer, breast cancer, cervical cancer, colon cancer, epithelial cancers, esophageal cancer, gastrointestinal cancers, gall bladder cancer, gynecological cancers, kidney cancer, laryngeal cancer, liver cancer, lung cancer, nose cancer, ovarian cancer, pancreatic cancer, rectum cancer, Schneeberg lung cancer, skin cancer, squamus cell and/or basal cell cancers, stomach cancer, testicular cancer, throat cancer, tongue cancer, urethral cancer, uterine cancer, vaginal cancer, cancer of the large intestine, cancer of the small intestine, cancer in the area of the mouth and on the lip, brain tumors (gliomas), connective tissue tumor, Ewing tumors, eye tumors, germ cell tumor, hypophysis tumor, osteolytic tumors and osteoblastic tumors, soft tissue tumors, urological tumors, Wilm's tumor, tumors of the small intestine, tumors of ear, nose and throat, head and neck tumors (tumors situated in the region of the neck, nose and ears), tumor of the eyelid, acute myeloid leukemia (AML), acute promyelocytic leukemia (APL), adenocarcinomas, acute leukemia, acoustic neurinoma, ampullary carcinoma, anal carcinoma, astrocytomas, basal cell carcinoma, brain metastases, breast carcinoma, bronchial carcinoma, Burkitt's lymphoma, Canine B-Cell Lymphoma, carcinoids, choroidal melanoma, chronic myelogenous leukemia (CML), colorectal carcinoma, colon carcinoma, craniopharyngiomas, corpus carcinoma, CUP syndrome, endometrial carcinoma, ependymoma, epithelial call-derived neoplasia (epithelial carcinoma), esophageal carcinoma, gall carcinomas, glioblastomas, hairy cell leukemia, head and neck squamous cell carcinoma, hematological neoplasias, hepatocellular carcinoma, Hodgkin's disease, Kaposi's sarcoma, liver metastases, leukemia, lymphomas, malignant lymphoma (Hodgkin/Non-Hodgkin), malignant melanoma, malignant neoplasma, malignomas of the gastrointestinal tract, medulloblastomas, melanoma, meningiomas, mycosis fungoides, myelomas, neurinoma, neuroblastoma, Non-Hodgkin's lymphomas, non-small cell bronchial carcinoma, oligodendroglioma, osteosarcoma, ovarian carcinoma, pancreatic carcinoma, papillary renal carcinoma, penile carcinoma, plasmacytoma, prostate carcinoma, rectal carcinoma, renal cell carcinoma, retinoblastoma, squamous cell carcinoma of the head and the neck, soft tissue sarcoma, spinocellular carcinoma, T-cell lymphoma (Mycosis fungoides), thymoma, thyroid carcinoma, tube carcinoma, urothelial carcinoma, vulvar carcinoma, wart appearance, and solid tumors.

In another embodiment, the disease is cancer, wherein the cancer comprises a neovasculature expressing PSMA.

In certain embodiments, the disease is prostate cancer, renal cell carcinoma, glioblastoma, colon cancer, gastric cancer, bladder cancer, pancreatic cancer, sarcoma, melanoma, skin cancer and lung cancer.

In other embodiments, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, complications associated with hypertension and/or heart failure, vascular organ damage, restenosis, cardiomyopathy, stroke, ischemic stroke, hemorrhagic stroke, reperfusion injury, renal reperfusion injury, ischemia, brain ischemia, ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, pneumonia, herpes virus, myalgias due to infection, influenza, autoimmune disease, graft vs. host reaction and allograft rejections, treatment of bone resorption diseases, osteoporosis, multiple sclerosis, angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy.

In certain embodiments, the subject is administered an additional therapeutic agent.

In another embodiment, the compound and the additional therapeutic agent are administered simultaneously or sequentially.

In certain embodiments, the subject is a human, rat, mouse, cat, dog, horse, sheep, cow, monkey, avian, or amphibian. In a further embodiment, the subject is a human.

In one embodiment, the nanoparticle composition has an $IC_{50}$ value ranging from about 0.1 to about 200 nM.

In a further embodiment, the nanoparticle composition has an $IC_{50}$ value ranging from about 0.5 to about 125 nM.

In one aspect, the invention provides a method of synthesizing a compound of formula II in claim 5, comprising the steps of:

a) reacting a compound of formula A:

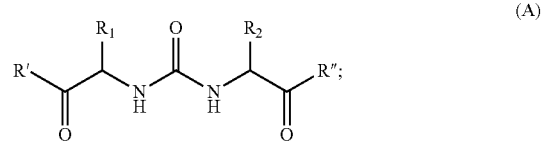

wherein, $R_1$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

$R_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

R' and R" are each independently —$OR_4$, —$SR_4$, —$SOR_4$, —$SO_2R_4$, —$N(R_3)S(O)_2$—$R_4$, —$N(R_3)(SO_2)NR_3R_4$, —$NR_3R_4$, —C(O)—O—$R_4$, —C(O)$R_4$, —C(O)$NR_3R_4$, or —$N(R_3)C(O)R_4$;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

with a compound of formula B:

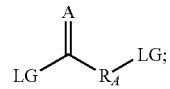

wherein

A is O, S, NH, N(alkyl) or N(aryl);

$R_A$ is optionally substituted alkyl, optionally substituted alkenyl or optionally substituted alkynyl, each containing heteroatoms selected from O, S, or N; and each LG is independently a leaving group; and b) reacting the product of step a) with a nanoparticle comprising a biologically active agent to form a composition of formula II.

Typical subjects to which compounds of the invention may be administered are mammals, particularly primates, especially humans. For veterinary applications, a wide variety of subjects are suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals are suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects are suitable for use such as mammalian, particularly primate such as human, blood, urine or tissue samples, or blood urine or tissue samples of the animals mentioned for veterinary applications.

Pharmaceutical Compositions and Kits

In certain aspect, the invention provides a kit comprising a nanoparticle composition, and instructions for use in treating cancer, wherein the nanoparticle composition comprises a) a prostate specific membrane antigen (PSMA) inhibitor; b) a linker, c) a biologically active agent; and d) a nanoparticle; or a nanoparticle composition of formula I:

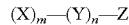

(I);

wherein
X is an organic small molecule PSMA inhibitor;
Y is an organic linker;
Z is a nanoparticle comprising a biologically active agent;
m is 1-1000 and
n is 1-1000.

In another aspect, the invention provides a pharmaceutical composition comprising a nanoparticle composition, and a pharmaceutically suitable excipient, wherein the nanoparticle composition comprises a) a prostate specific membrane antigen (PSMA) inhibitor; b) a linker, c) a biologically active agent; and d) a nanoparticle; or a nanoparticle composition of formula I:

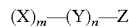

(I);

wherein
X is an organic small molecule PSMA inhibitor;
Y is an organic linker;
Z is a nanoparticle comprising a biologically active agent;
m is 1-1000 and
n is 1-1000.

The present invention also provide packaged pharmaceutical compositions comprising a pharmaceutical acceptable carrier and a composition of the invention. In certain embodiments the packaged pharmaceutical composition will comprise the reaction precursors necessary generate the composition of the invention upon combination of the biologically active agent.

In certain preferred embodiments, the invention provides a kit according to the invention contains a composition of the invention, in combination with a pharmaceutically acceptable carrier. The composition and carrier may be provided in solution or in lyophilized form. When the composition and carrier of the kit are in lyophilized form, the kit may optionally contain a sterile and physiologically acceptable reconstitution medium such as water, saline, buffered saline, and the like.

The kit may provide a composition of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the composition is in lyophilized form, the kit may optionally contain a sterile and physiologically acceptable reconstitution medium such as water, saline, buffered saline, and the like. The amounts of composition, auxiliary molecule, and/or other reagents in this embodiment are optimized in accordance with the methods set forth above.

The pharmaceutical compositions of the present invention comprise a therapeutically effective amount of a composition of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active composition can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As is well understood in the medical arts a therapeutically effective amount of a composition of this invention will be at a reasonable benefit/risk ratio applicable to any medical treatment.

Binding of PEGylated Inhibitor, FPPi, to PSMA

The PSMA inhibitor PSMAi1 is ideally suited for this nanoparticle application due to the presence of a primary amine that allows for amide bond formation with carboxyl groups present on PEG monomers. Previously it had been demonstrated that urea-based PSMA inhibitors bearing structural homology to PSMAi1 inhibited NAAG hydrolysis with the $IC_{50}$ value range of 1-10 nM (Kozikowski, A. P., ET AL. J Med Chem, 47: 1729-1738, 2004). On this basis, PSMAi1 was coupled to fluorescently labeled 3400 MW PEG as outlined in Scheme 1. The presence of the fluorescein at the opposite end of the PEG monomer allowed a way to follow the reaction and subsequent purification of the product by dialysis. FPPi inhibited PSMA hydrolysis of NAAG with an $IC_{50}$ value between 1 and 10 nM. While it was expected that the addition of the large PEG moiety to increase the $IC_{50}$ value, the $IC_{50}$ value was still in the same range suggesting that a) the addition of PEG did not pose a steric hinderance and b) FPPi possessed sufficient affinity for PSMA to justify further studies in which the PEGylated inhibitor would be introduced onto the surface of nanoparticles. PEG itself was not observed to bind to affect the enzymatic of PSMA (data not shown).

Nanoparticle Formulation

Figure 3:
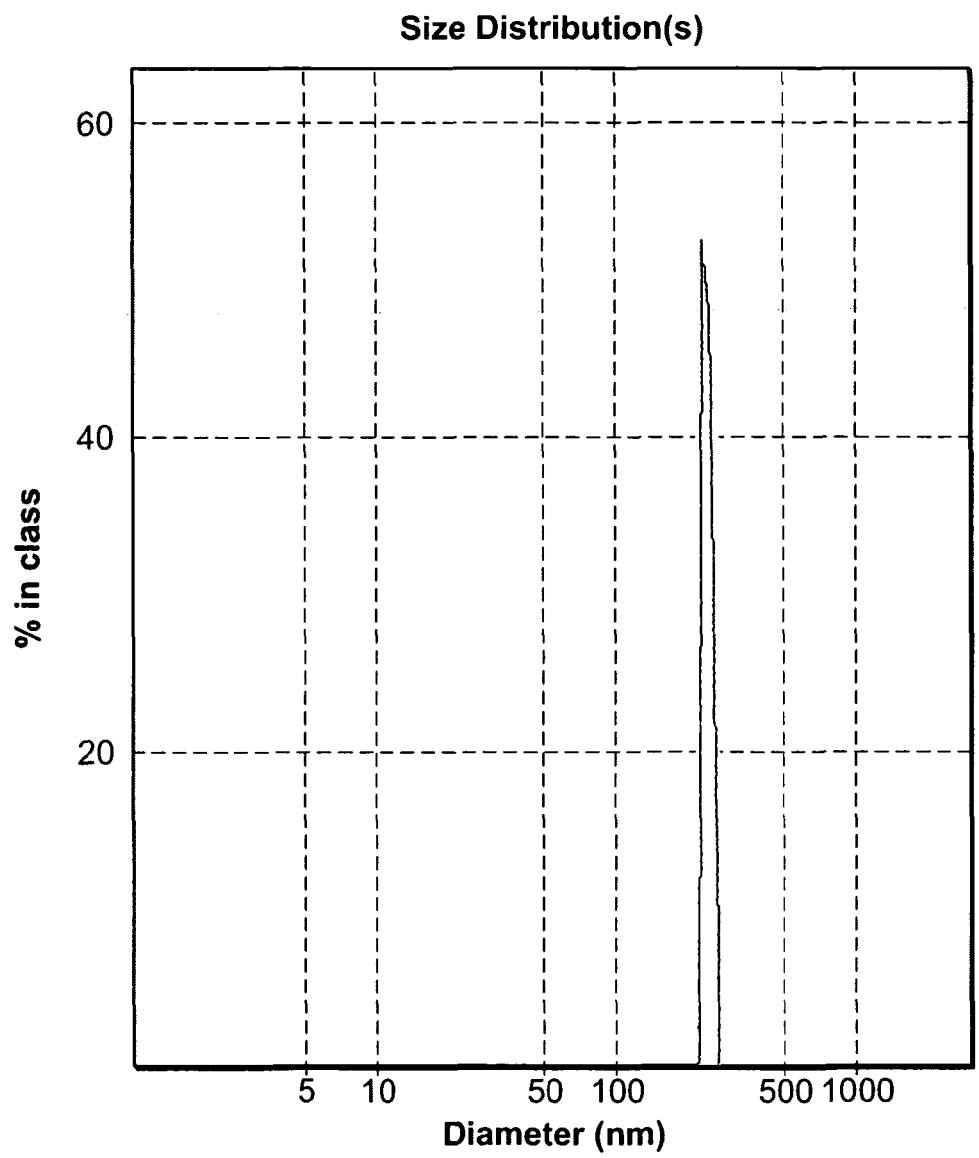
FIG. 3: Size distribution of nanoPSMAi2 as obtained by Light Scattering. The number average of size was estimated to be 222 nm. As observed, the nanoparticles are monodisperse with a polydispersity index of 0.131.

The synthesis of the PSMA-targeted nanoparticle was based on a strategy whereby the PLA-PEG-PLA copolymer partitions such that the PLA region would comprise the core of the nanoparticle while the water-soluble but acetone-insoluble PEG region would be in the aqueous layer and thus emerge on the surface. This approach has been defined earlier and provides stealth attributes to the nanoparticle (Farokhzad, O. C., et al. Proc Natl Acad Sci USA, 103: 6315-6320, 2006; Hu, Y., et al. Biomaterials, 24: 2395-2404, 2003). Since the tricarboxylic acid containing PSMA inhibitor is highly hydrophilic, it would be expected to orient itself toward the surface of the nanoparticle during formulation. In order to facilitate such orientation, it was conjugated to the PEG-PCL copolymer such that the PCL would integrate into the nanoparticle matrix and the PEG and hydrophilic PSMAi2 would orient toward the surface. On this basis, the polymer bound PSMA inhibitor (polyPSMAi2) was synthesized as outlined in Scheme 2. $^1$H-NMR and ESI analysis confirmed correct structure. Nanoparticles incorporating polyPSMAi2 (nanoPSMAi2) and docetaxel were then formulated using the solvent evaporation technique. NanoPSMAi2 particles were found to be monodisperse with a polydispersity index of 0.131 and had an average size of approximately 222 nm (FIG. 3). The loading efficiency of docetaxel was observed to be in the range of 40±2% over multiple experiments. The surface density of the PSMA inhibitor was computed to be $2.23 \times 10^{17}$ molecules/m$^2$ of surface area of the nanoparticles (~30,000 inhibitor molecules/nanoparticle).

Nanoparticle Binding as Observed by NAAG Assay

Figure 2A:
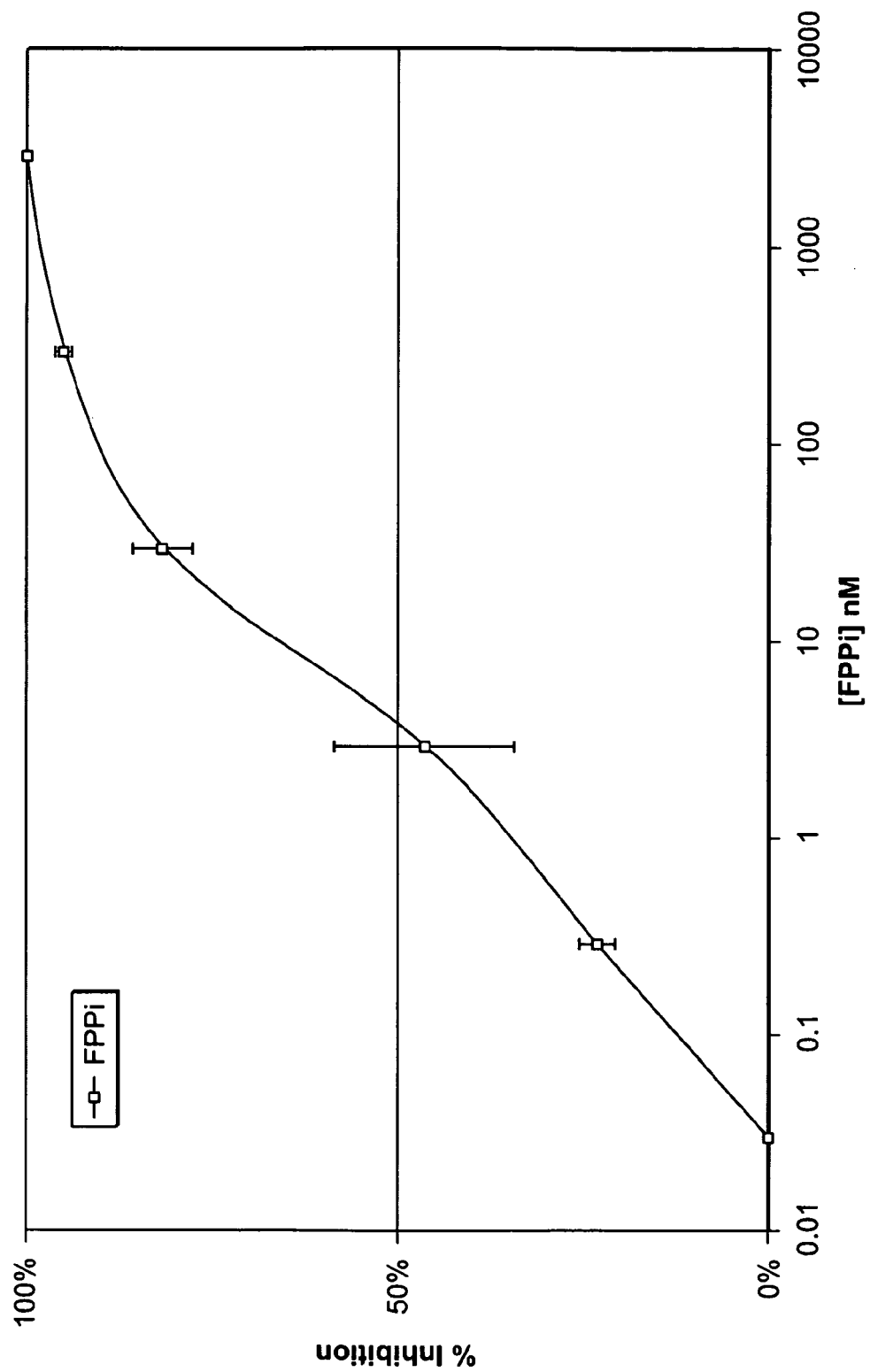
FIG. 2: (a) Inhibition of activity of PSMA by FPPi and PEG. FPPi inhibits the activity of PSMA with an IC$_{50}$ in the range of 10 to 100 ng/mL. In contrast, PEG inhibits the activity of PSMA by no more than 10% at its highest concentration of FPPi tested suggesting specific inhibition (data not shown) (b) PSMA inhibition by polyPSMAi2 when in free and nanoparticle form. There is a slight increase in the IC$_{50}$ when bound to the nanoparticle due to steric hindrance.
Figure 2B:
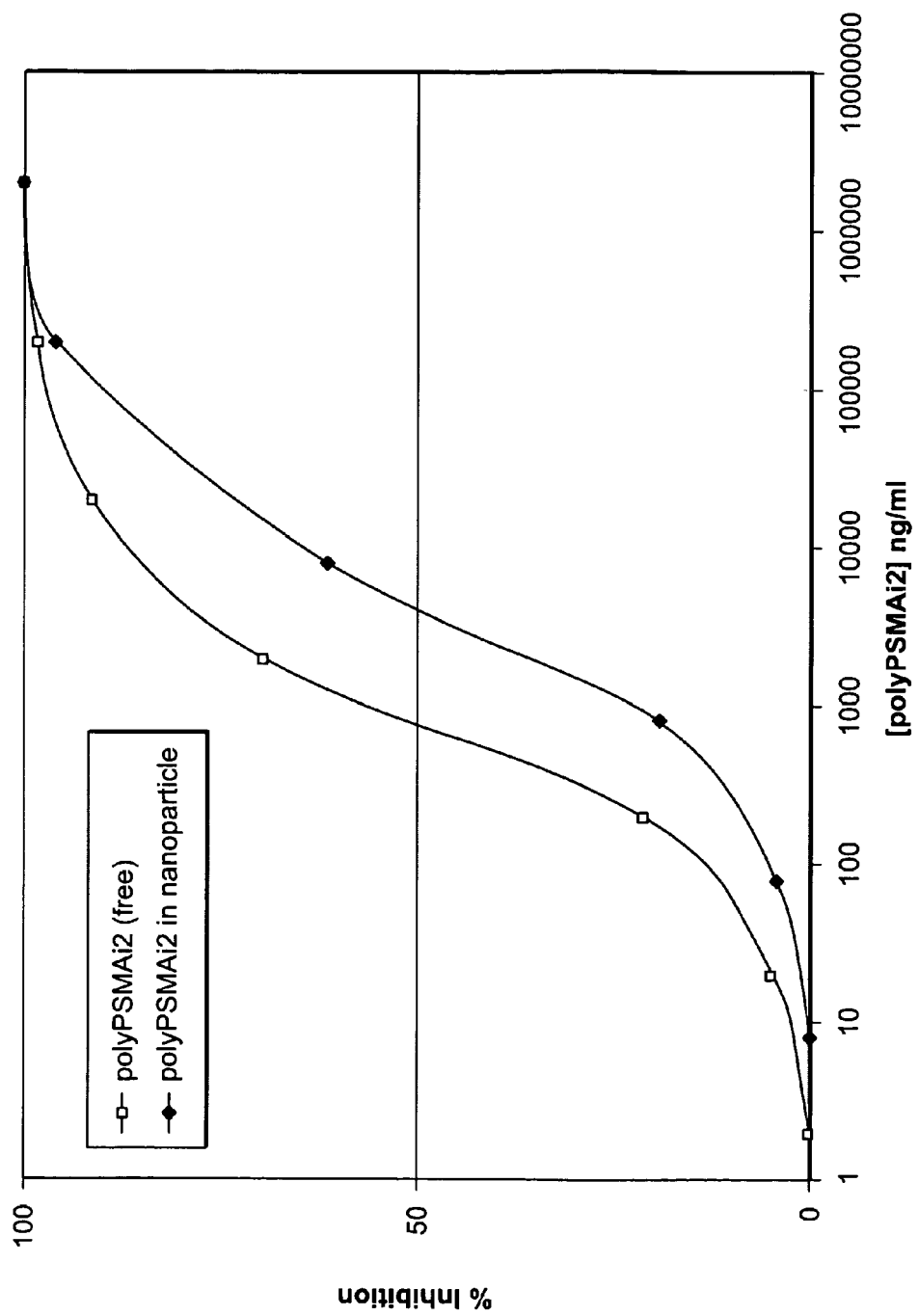

Nanoparticles formulated with a surface decorated with small-molecule PSMA inhibitors were tested for activity against PSMA from LNCaP homogenate via the NAAG assay as described above. Initial testing was carried out with polyPSMAi2 which was observed to inhibit the activity of PSMA at an $IC_{50}$ of close to 1000 ng/mL. Subsequently, polyPSMAi2 was incorporated into the nanoparticle matrix to give nanoPSMAi2, which was also observed to inhibit PSMA activity. A shift of the binding curve to the right was observed, FIG. 2b, suggesting that when tethered on the surface of the nanoparticle, the inhibitor is unable to bind to PSMA with the same affinity as it could when in the polymeric form.

Observation of Nanoparticle Binding by Fluorescence

To evaluate whether the nanoPSMAi2 particles exhibited enhanced binding to PSMA-positive prostate cancer cells compared to nontargeted nanoPEG particles, the respective particles were labeled with Texas Red. This was accomplished by incorporating a Texas Red labeled PEG-PCL copolymer (polyTR) into the nanoparticles. The incorporation of Texas Red (MW 625 Da) labeled polymers was not expected to alter the size of the nanoparticles significantly. Since it is known that cells can nonspecifically endocytose polymer nanoparticles (Chavanpatil, M. D., et al. J Nanosci Nanotechnol, 6: 2651-2663, 2006), the concentration of the nanoparticles was kept low. The cells were also incubated with the nanoparticle suspension under agitation to further minimize endocytosis.

A confocal section of the nontargeted Texas Red labeled nanoPEG particles exhibited no red fluorescence as would have been observed with nanoparticles binding to cells. In contrast, the targeted nanoPSMAi2 particles undergo endocytosis after 15 min of incubation. Previously it was demonstrated that PSMA becomes internalized following binding by antibodies and small-molecule PSMA inhibitors (Rajasekaran, S. A., et al. Mol Biol Cell, 14: 4835-4845, 2003). PSMA can also undergo internalization and be recycled in the absence of ligand binding. Herein, minimal to no endocytosis was observed in the case of the nontargeted particles. Thus, it appears that the endocytosis is mediated by nanoPSMAi2 particle binding to PSMA leading to subsequent internalization by endocytosis.

In addition to confocal microscopy, fluorescence microscopy was undertaken with the intention of observing nanoparticle binding on the cell surface. The data obtained suggest that binding on the cell surface is highly dependent on the presence of a targeting moiety on the surface of the nanoparticle. As expected, minimal nonspecific surface binding is observed in the case of the nontargeted nanoparticles. In contrast, a high number of PSMA-targeted nanoparticles are seen on the cell surface away from the nuclei.

In Vitro Cytotoxicity to PSMA Expressing Human Prostate Cancer Cells

Figure 4:
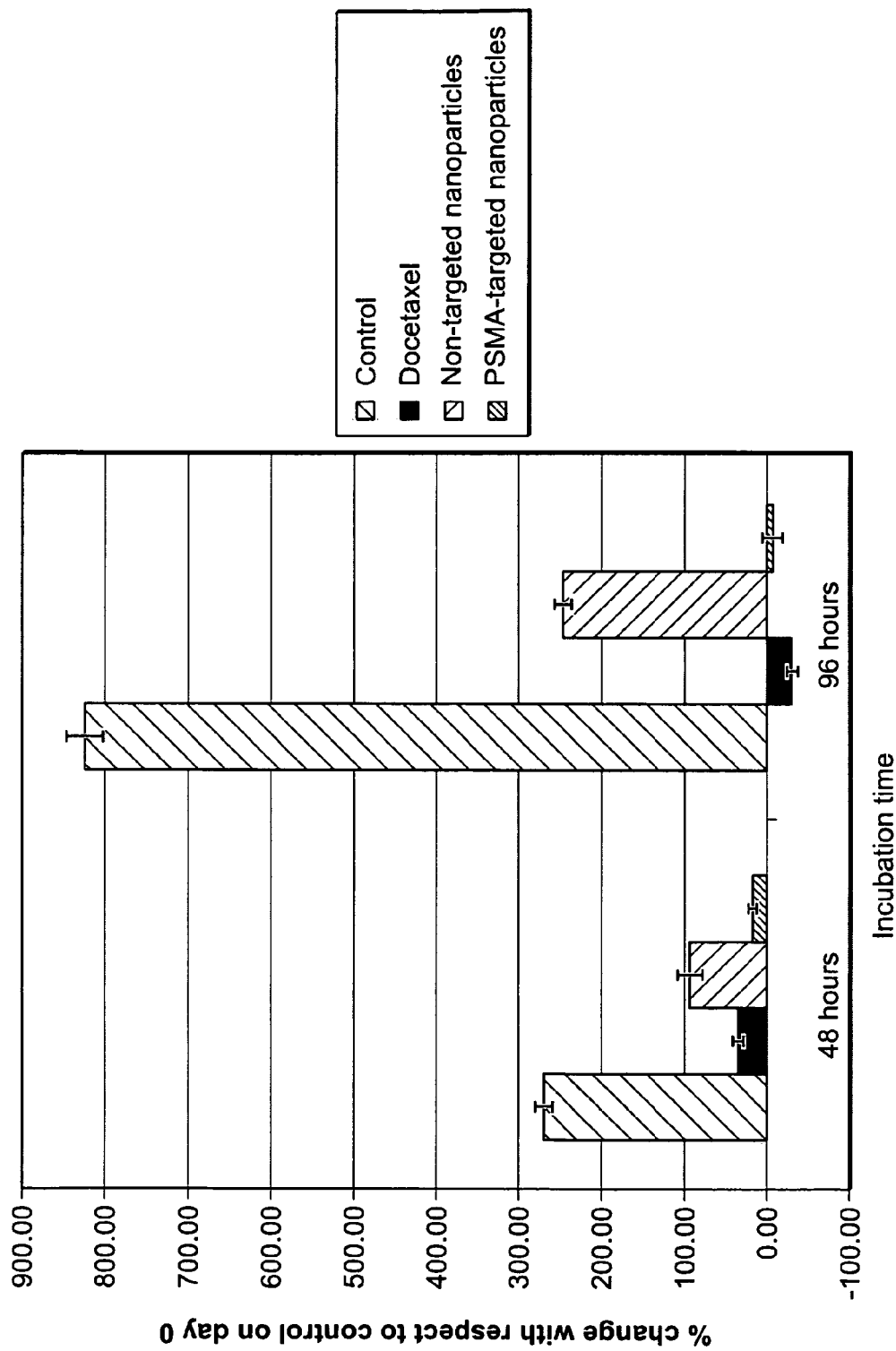
FIG. 4: In vitro toxicity of nontargeted and targeted nanoparticles after a 15 min incubation at a docetaxel concentration equivalent of 100 nM. After 48 hour incubation, the treated arms show regression in growth. The effect is magnified with the higher incubation time of 96 hours where the controls have expanded considerably, the nontargeted nanoparticles demonstrate regression and the PSMA-targeted nanoparticles not only induce regression, but also reduce the overall cell number. Docetaxel was used as the control.

Previously, Farokhzad et al compared the in vitro cytotoxicity of docetaxel encapsulated PSMA-targeted RNA aptamer nanoparticle to a nontargeted nanoparticle to LNCaP cells (Farokhzad, O. C., et al. Proc Natl Acad Sci USA, 103: 6315-6320, 2006.). This group demonstrated that 72 hrs after a 30 min exposure the viability of LNCaP cells exposed to the PSMA-targeted particles was 20% higher than the nontargeted particles. The cytotoxicity of the nontargeted particles in that study was ascribed to a combination of nonspecific uptake and to the expected nonspecific release of docetaxel from the particle into the media over the exposure period. To evaluate whether incorporation of the urea-based PSMA inhibitor enhanced the cytotoxicity of the nanoparticle to PSMA expressing cells in vitro, we performed similar assays to those of Farokhzad et al and compared the effects of the docetaxel loaded nanoPSMAi2 particles to those of the untargeted nanoPEG particles and docetaxel alone. Following determination of the amount of docetaxel loading in the particles, PSMA-expressing LNCaP human prostate cancer cells were exposed to equimolar amounts (i.e. 100 nM) of loaded nanoparticles or free docetaxel. To minimize the effects of nonspecific endocytosis, cells were only exposed to test compounds for 15 min at which time cells were washed and then placed in drug free media. Cell counts were determined by converting absorbance from MTT assay to cell number based on a standard curve of absorbance from MTT assay of known amounts of LNCaP cells. In this assay, 48 hrs following exposure, the growth of cells exposed to the nontargeted nanoPEG particles was inhibited by 65% while cell growth was inhibited 89% by docetaxel and 95% by the nanoPSMAi2 particles. At 96 hrs after exposure to the nontargeted particles cells continued to grow but overall cell growth was inhibited 70% compared to control. In contrast, at this time point exposure to the nanoPSMAi2 particles resulted in a ~10% decrease in the absolute cell number compared to starting cell number at day 0, FIG. 4. These results demonstrate the increased antitumor efficacy that can be achieved by incorporating a cell surface protein specific binding ligand onto the surface of a docetaxel encapsulated nanoparticle. No efficacy was observed in any of the above-mentioned systems at a concentration of docetaxel of 10 nM.

In these studies it has been established that a nanoparticle system decorated with a small-molecule PSMA inhibitor on the surface enhances binding to PSMA. This is the first time in our knowledge that such a system has been designed with the use of small-molecule ligands for PSMA as a specificity-conferring mechanism. The approach is comparable to the approach of Farokhzad et al. who characterized a docetaxel encapsulated PSMA-targeted RNA aptamer based nanoparticle for in vitro toxicity and for efficacy following intratumoral injection in vivo. Those authors selected a previously described RNA aptamer A10, which is a competitive inhibitor with a reported $K_i$ for PSMA of 11.9 nM (Lupold, S. E., et al. Cancer Res, 62: 4029-4033, 2002). The urea-based inhibitor used to target our particles has a $K_i$ value in a similar range. Other groups have conjugated anti-PSMA antibodies to nanoparticles in order to generate systems that could be used for both imaging and therapeutic applications (Gao, X., et al. Nat Biotechnol, 22: 969-976, 2004).

Using a small-molecule inhibitor based system has certain unique advantages. First, the chemistry can be more controlled because unlike antibodies or aptamers, small-molecules can be synthesized with higher purity, accuracy, efficiency and economy. Another reason as compared to antibodies and aptamers is that unlike antibodies, small-molecules do not need to form tertiary structures to facilitate binding. Thus stability during formulation, which can be a big factor, is not an issue in this case. The use of a small-molecule inhibitor is advantageous since it has a lower exclusion space suggesting that up to 30,000 inhibitor molecules can be loaded on the surface (as observed in this study) thus maximizing the possibility of binding. And finally, in terms of future in vivo experiments, small-molecules are less likely to elicit an immune response compared to large antibodies, and therefore such nanoparticles should provide long circulatory half lives in the body upon injection.

The results demonstrate that PSMA-targeted nanoparticles enhance cytotoxicity via binding to PSMA protein present on the surface of prostate cancer cells.

EXAMPLES

The present invention is further illustrated by the following examples which should not be construed as limiting in any way. The practice of the present invention will employ, unless otherwise indicated, conventional techniques, which are within the skill of the art. Such techniques are explained fully in the literature.

General Procedures.

All reactions were performed under a nitrogen atmosphere unless otherwise noted. Solvents and chemicals obtained from commercial sources were of analytical grade or better and used without further purification. All experiments were performed in duplicate or triplicate to ensure reproducibility. Analytical thin-layer chromatography (TLC) was performed using Aldrich aluminum-backed 0.2 mm silica gel Z19, 329-1 plates and visualized by ultraviolet light (254 nm), $I_2$ and 1% ninhydrin in EtOH. Flash chromatography was performed using silica gel purchased from Bodman (Aston Pa.), MP SiliTech 32-63 D 60 Å. In most cases product isolation consisted of removing of the solvent from the reaction mixture, extracting with an organic solvent, washing with water and brine, drying with anhydrous sodium sulfate, filtering, and concentrating the filtrate. The use of such workup conditions will be indicated by the phrase "product isolation" (which is followed, in parentheses, by the extracting solvent). Purification in most cases was achieved by flash chromatography and is signified by the term "flash chromatography" (which is followed, in parentheses, by the elution solvent used). Melting points were measured using a MeI-Temp apparatus and are uncorrected. $^1$H NMR spectra were recorded on either a Varian Mercury 400 MHz or on a Bruker Ultrashield™ 400 MHz spectrometer. Chemical shifts (δ) are reported in ppm downfield by reference to proton resonances resulting from incomplete deuteration of the NMR solvent. Low resolution ESI mass spectra were obtained on a Bruker Daltonics Esquire 3000 Plus spectrometer. Higher-resolution FAB mass spectra were obtained on a JOEL JMS-AX505HA mass spectrometer in the mass spectrometer facility at the University of Notre Dame. Optical rotation was measured on a Jasco P-1010 polarimeter. Infrared spectra were obtained on a Bruker Tensor 27 spectrometer.

Materials and Methods

Fluor-PEG-NHS (Nektar Therapeutics, AL) was used as purchased. All other polymers were purchased from Polymer Source (Canada). They were used as instructed by the manufacturer. Tetronic 904 surfactant was a kind gift from BASF (Florham Park, N.J.). Unless otherwise described, all chemicals were purchased from Sigma Aldrich (Saint Louis, Mo.), and used without any further purification.

Cell Lines

LNCaP human prostate cancer cell lines used in this study were purchased from ATCC and grown in RPMI 1640 supplemented with 10% fetal bovine serum (HyClone, UT), 1% penicillin-streptomycin (Mediatech, VA), and 1% L-glutamine (Mediatech, VA). The cells were maintained at 37° C. in a humidified 5% $CO_2$-containing incubator.

Example 1

Synthesis of PEGylated PSMA Inhibitor (FPPi)

To a solution of 2-[3-(5-amino-1-carboxypentyl)-ureido]-pentanedioic acid (PSMAi1) (38 mg, 88.2 µmol in 1.5 mL dimethylformamide) was added diisopropylethylamine (0.3 mL, 1.72 mmol) followed by Fluor-PEG-NHS (MW ~3400) solution (150 mg, 44.11 µmmol in 1 mL dimethylformamide) at 0° C. (Scheme 1). After 5 min, the solution was allowed to warm to room temperature and was kept for 16 h under an argon atmosphere. The solution was concentrated under high vacuum to yield a yellow residue. The residue was dissolved in 10 mL of methylene chloride and washed with 5×10 mL of water to remove the starting material. Organic fractions were combined and concentrated under reduced pressure to yield a yellow solid. The solid FPPi was further purified by dialysis against water using a MW 1000 cutoff membrane (SpectraPOR CE, CA) using 3 solvent changes over 4 days, followed by lyophilization for further use. FPPi was characterized by $^1$H-NMR.

Scheme 1

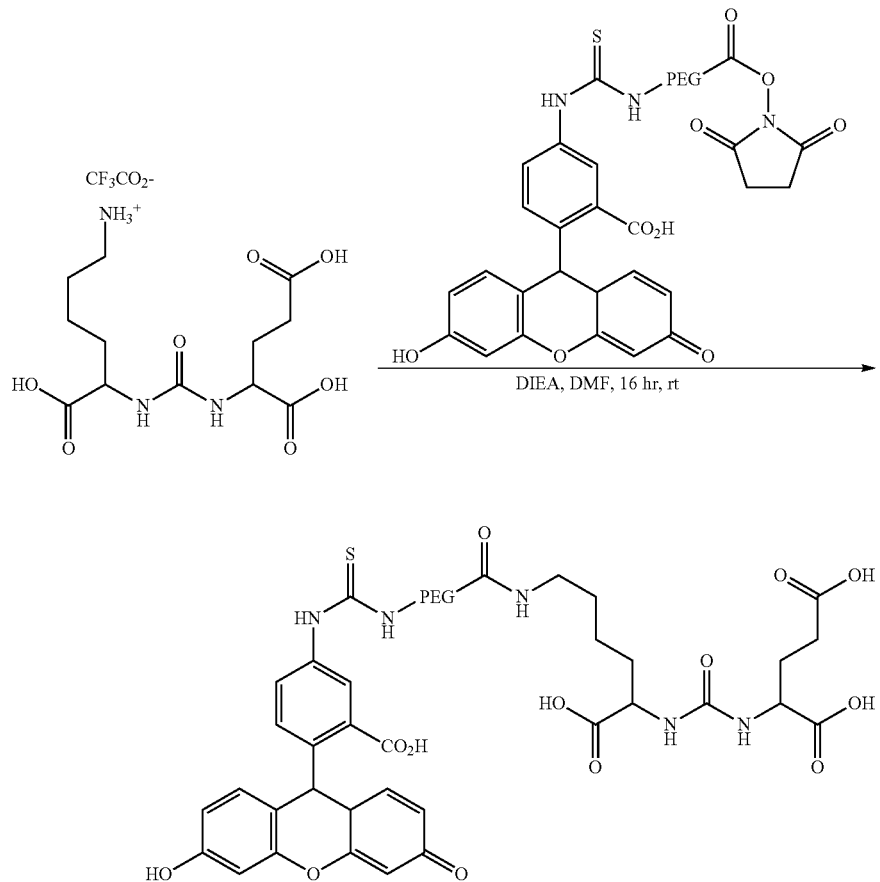

Example 2

Synthesis of NHS ester of PSMA inhibitor, 2-(3-{1-carboxy-5-[7-(2,5-dioxo-pyrrolidin-1-yloxycarbonyl)-heptanoylamino]-pentyl}-ureido)-pentanedioic acid (PSMAi2)

2-{3-[5-[7-(2,5-dioxo-pyrrolidin-1-yloxycarbonyl)-heptanoylamino]-1-(4-methoxy-benzyloxycarbonyl)-pentyl]-ureido}-pentanedioic acid bis-(4-methoxy-benzyl)ester (30 mg, 0.032 mmol) was dissolved in 5 mL 1:1 TFA:methylene chloride solution and was kept at room temperature for 3 h (Scheme 2). The resulting solution was evaporated under reduced pressure. The colorless solid residue was washed 5×1 mL of diethyl ether. The residue was dissolved in 10 mL chloroform and extracted with 3×10 mL water to remove impurities. The organic layer was evaporated to dryness to get the desired product, PSMAi2. Yield: 11.4 mg, 62%. Product was characterized by $^1$H NMR and MALDI-TOF.

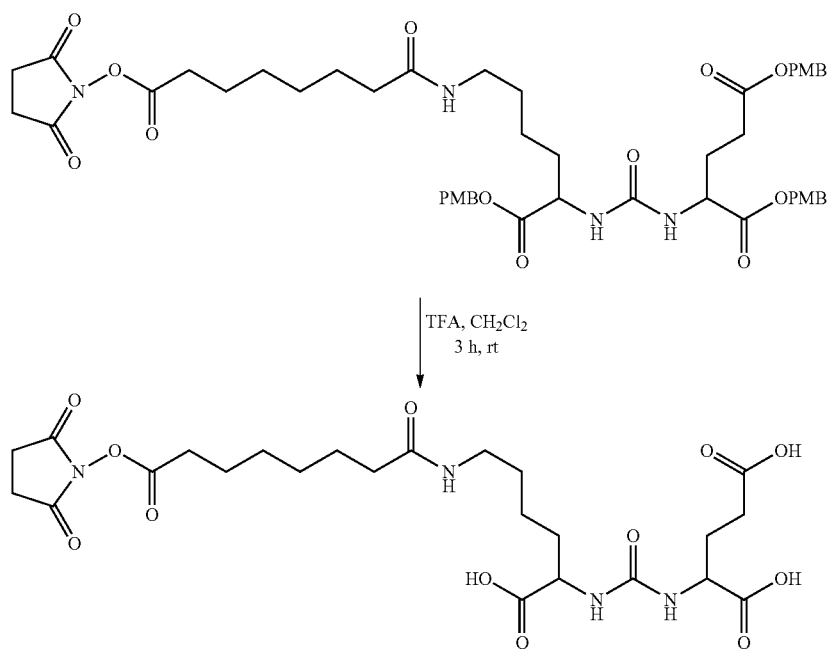

Scheme 2

Example 3

Coupling of PSMAi2 to PEG-PCL (polyPSMAi2)

PSMAi2 (11.4 mg, 20 µmol) was dissolved in 3 mL dimethylformamide (DMF). PEG-PCL (MW~25000, ratio of PEG:PCL is approximately 1:4 by weight) (257 mg, 10 µmol in 5 mL DMF) was added at room temperature followed by diisopropylethylamine (0.5 mL) and was kept at room temperature for 48 hr (Scheme 3). The resulting solution was concentrated under vacuum and a white solid was then precipitated by dropwise addition to water. The precipitate was redissolved in DMF, precipitated again in water and then washed with 5×10 mL methanol. All organic fractions were combined together and evaporated under reduced pressure. The desired product was obtained as a colorless solid and characterized by $^1$H-NMR.

Scheme 3

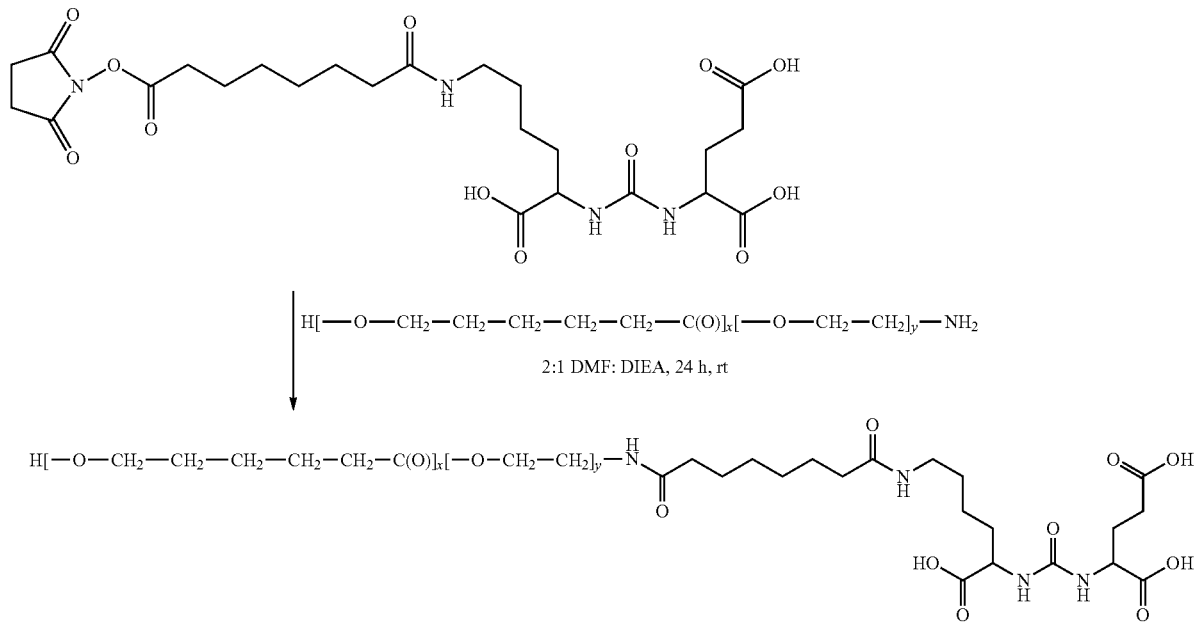

Example 4

Synthesis of Texas Red Labeled PEG-PCL (polyTR)

115 mg (4.6 μmol) of PEG-PCL was dried overnight under high vacuum. Texas Red sulfonyl chloride (3 mg, 4.8 μmmol in 1 mL of dry DMF and 0.1 mL diisopropylethylamine) was then added to PEG-PCL under $N_2$ with vigorous stirring. The reaction was allowed to proceed overnight in the dark at room temperature. Separation of the labeled copolymer was achieved by precipitation in water. Further purification was achieved by redissolving in DMF followed by reprecipitation and washing with 5×10 mL of water. Final product, polyTR was obtained as a lyophilized solid and characterized by fluorescence.

Example 5

Formulation and Characterization of Nanoparticles

Polymer nanoparticles were formulated as a modification of the solvent evaporation technique as described previously (Hu, Y., et al. Biomaterials, 24: 2395-2404, 2003). Briefly, nanoparticles were prepared by initially dissolving 5 μL of 100 mg/mL docetaxel in DMSO into 5 mL of a 10 mg/mL solution of PLA-PEG-PLA. PLA-PEG-PLA comprised of a 1.2 kDa chain of PEG flanked by a 6.3 kDa chain of PLA on either side. The polymer was nanoprecipitated along with the encapsulated drug by slowly pipetting into 10 mL of a 0.4% solution of Tetronic 904 with vigorous agitation for approximately 15 min. Subsequently, the acetone was evaporated under a rotary evaporator taking care to prevent excessive bumping in the round bottomed flask. The polymer nanoparticles were separated by centrifuging at 10000 g for 15 min. This was repeated once. The nanoparticles were finally redispersed in Tetronic 904 depending on the desired final concentration of docetaxel. Targeted nanoparticles were formulated in a similar fashion with the exception that the polyPSMAi was incorporated into the nanoparticle by initially dissolving it with PLA-PEG-PLA in acetone such that a known ratio of polyPSMAi to PLA-PEG-PLA was maintained. When fluorescent particles were desired, polyTR was added in a manner akin to the polyPSMAi.

Particle size was determined using a Zetasizer (Malvern Zetasizer 3000, Malvern, UK). Each analysis lasted until a suitable value for the auto-correlation function was obtained and was performed at 25° C. The measurement was repeated three times with the average size across the measurements being reported.

Surface coverage of PSMA inhibitor on the nanoparticles was determined by $^1$H-NMR. Targeted nanoparticles were dissolved in $CHCl_3$ and NMR spectra were obtained. The ratio of the proton peak at 5.2 ppm from the polycaprolactone to the peak at 4.1 from the polylactic acid provided us with a measure of integration of the polyPSMAi into the PLA-PEG-PLA copolymer mesh. Given that the yield of the reaction in which the PSMA inhibitor was conjugated to PEG-PCL was previously evaluated, it was possible to determine the number of PSMA inhibitor molecules per gram of polymer. With the assumption that the particles have a specific gravity of 1, and with knowledge of the particle size, the surface coverage can be computed.

Example 6

Determination of Drug Loading

High performance liquid chromatography (HPLC) analysis was carried out using a C-18 column on a reversed phase HPLC system (Waters, MA). A dual-absorbance detector (Waters 2457) was used for analysis at 215 nm and 254 nm. The mobile phase consisted of solvent A, 0.1% TFA in water and solvent B, 0.1% TFA in acetonitrile. Gradient elution from 20% B to 100% B over 22 minutes was used for chromatography. Chrom Perfect software supplied with the HPLC system was used for data analysis. A calibration curve for docetaxel was initially generated by injecting known amounts of docetaxel and measuring the area under the elution curve at 254 nm. The area under the curve was fitted to the injection amount in a linear fashion. To determine the amount of encapsulated drug in the nanoparticles, a known amount of drug-loaded nanoparticles was dissolved in DMSO followed by injection onto the HPLC. The area under the curve of the elution profile corresponding to docetaxel was measured and the amount of docetaxel was estimated using the standard curve. Using the initial amount loaded onto the nanoparticles, the loading efficiency was computed.

Example 7

N-acetylated-aspartyl-[3H]glutamic Acid (NAAG) Assay for PSMA Activity

The NAAG assay involves measuring the cleavage of 50 nM NAAG by PSMA as defined in earlier work (Denmeade, S. R., et al. Prostate, 54: 249-257, 2003), in which the tritiated glutamic acid is released after hydrolysis. The reaction was carried out in a microfuge tube. At the desired time point, a known volume of the NAAG containing released [3H] glutamic acid was added to an ion-exchange column. The released [3H]glutamic acid binds to the column and is eluted by using 0.1 M formic acid. Degree of release of [3H]glutamic acid was measured by scintillation counting and is a direct measure of the release of product after enzymatic reaction. LNCaP cell homogenate containing 2.8 ug/mL of protein was used as the source of PSMA for inhibition studies. PSMA-containing LNCaP homogenates were incubated with either inhibitor, nontargeted nanoparticles or targeted nanoparticles. The $IC_{50}$ value, as obtained from this study, is a measure of 50% inhibition of the activity of PSMA as compared to the activity in the absence of inhibitor.

Example 8

Confocal Microscopy

LNCaP cells were incubated with Cell Tracker Green (Molecular Probes, OR) at a concentration of 5 mM in buffer for 15 min, after which they were washed with media to remove unreacted dye. The cells were then stripped off the flask by using a final concentration of 2.5 mM of EDTA for 15 min. Cells were collected, spun down, resuspended in media and stored in the incubator for 15 min followed by incubation with targeted or untargeted nanoparticles. Both nanoparticles were labeled with Texas Red. The degree of fluorescence from both nanoparticle systems was estimated by measurement of fluorescence of a known concentration of nanoparticles under a fluorescence plate reader (DTX880, Beckman Coulter, CA). Cells were separated from the nanoparticles by centrifuging at 300 g for 5 min. Spinning was repeated to remove all unbound nanoparticles from the cell suspension, following which cells were plated on glass bottom petridishes (MatTek Corporation, MA) and visualized using a Utraview LCI (Perkin Elmer, MA) confocal microscope equipped with Spinning Nipkow disk with microlenses. Cells were viewed using a 100× objective. Images were captured in the temporal module using a LSI-cooled 12-bit CCD camera at 488 nm and 654 nm respectively. Images were processed using the NIH ImageJ software (http://rsb.info.nih.gov/ij/download.html).

Example 9

Fluorescence Microscopy

LNCaP cells were stained with 4',6-diamidino-2-phenylindole (DAPI) (Invitrogen, CA) for 5 min following which the excess dye was removed. Further incubation with nanoparticles was undertaken as described above for confocal microscopy. Cells were mounted on slides followed by imaging using a Nikon Eclipse E800 system (Santa Clara, Calif.) under 100× magnification. Three representative fields per slide with two slides for each condition were used.

Example 10

In Vitro Toxicity of Nanoparticles

Cytotoxicity assays were performed as described previously (Denmeade, S. R., et al. J Natl Cancer Inst, 95: 990-1000, 2003). Approximately 20,000 LNCaP cells were seeded in 96-well plates and permitted to attach for two days. These cells were then incubated with 100 µL of a suspension of docetaxel loaded nanoparticles to a final concentration of 100 nM docetaxel. After a 15 min exposure, the media and nanoparticles in all of the wells were carefully removed by pipetting to minimize cell detachment, followed by gentle washing with 200 µL of media. Cells were then incubated in media at 37° C. and at the end of 48 hours and 96 hours, effects on cell growth were determined using the MTT assay (Promega, WI) according to manufacturer's instructions.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

The contents of all cited references (including literature references, issued patents, published patent applications) as cited throughout this application are hereby expressly incorporated by reference.

What is claimed is:
1. A nanoparticle composition comprising formula I:

$$(X)_m-(Y)_n-Z \qquad (I);$$

wherein,
X is a prostate specific membrane antigen (PSMA) inhibitor that is a compound of formula II,

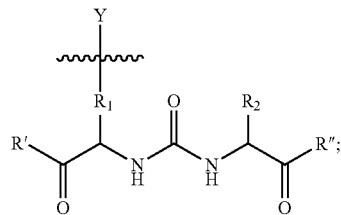

(II)

wherein,
$R_1$ is $(CH_2)_p$—$NR_3$—Y, wherein p is 1-6;
$R_2$ is selected from the group consisting of optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, and optionally substituted carbocyclic;

R' and R" are each independently selected from the group consisting of —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O—R$_4$, —C(O)R$_4$, —C(O)NR$_3$R$_4$, and —N(R$_3$)C(O)R$_4$;

R$_3$ and R$_4$ are each independently selected at each occurrence from the group consisting of: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; and optionally substituted carbocyclic;

a pharmaceutically acceptable salt thereof;

Y is

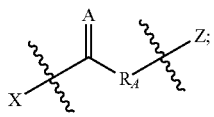

wherein

A is selected from the group consisting of O, S, NH, N(alkyl) and N(aryl); and

R$_A$ is (CH$_2$)$_r$-Q-Z;

Q is CO, C(O)O, C(O)NH, C(O)NR$_B$, OCO, OC(O)O, OC(O)NH, OC(O)NR$_B$, NHCO, NHC(O)O, NHC(O)NH, NHC(O)NR$_B$, NR$_B$CO, NR$_B$C(O)O, NR$_B$C(O)NH, NR$_B$C(O)NR$_B$, CS, C(S)O, C(S)NH, C(S)NR$_B$, OCS, OC(S)O, OC(S)NH, OC(S)NR$_B$, NHCS, NHC(S)O, NHC(S)NH, NHC(S)NR$_B$, NR$_B$CS, NR$_B$C(S)O, NR$_B$C(S)NH, NR$_B$C(S)NR$_B$;

each R$_B$ is independently optionally substituted alkyl or optionally substituted aryl; and r is 3-20;

Z is a nanoparticle m is 1-1000, and n is 1-1000, and a biologically active agent.

2. The composition of claim 1, wherein the biologically active agent is encapsulated in the nanoparticle.

3. A kit comprising a nanoparticle composition of claim 1, and instructions for use in treating cancer.

4. A pharmaceutical composition comprising a nanoparticle composition of claim 1, and a pharmaceutically suitable excipient.

5. The nanoparticle composition of claim 1, wherein the biologically active agent is docetaxel.

6. The nanoparticle composition of claim 1, wherein the nanoparticles are capable of binding PSMA.

7. A nanoparticle composition of formula I:

(X)$_m$—(Y)$_n$—Z          (I);

wherein

X is an organic small molecule PSMA inhibitor inhibitor that is a compound of formula II,

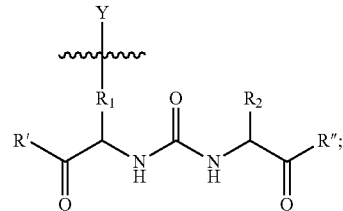

wherein,

R$_1$ is (CH$_2$)$_p$—NR$_3$—Y, wherein p is 1-6;

R$_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, or optionally substituted carbocyclic;

R' and R" are each independently —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O—R$_4$, —C(O)R$_4$, —C(O)NR$_3$R$_4$, or —N(R$_3$)C(O)R$_4$;

R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

or a pharmaceutically acceptable salt thereof;

Y is

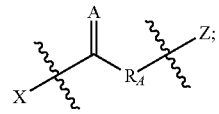

wherein

A is O, S, NH, N(alkyl) or N(aryl); and

R$_A$ is (CH$_2$)$_r$-Q-Z;

Q is CO, C(O)O, C(O)NH, C(O)NR$_B$, OCO, OC(O)O, OC(O)NH, OC(O)NR$_B$, NHCO, NHC(O)O, NHC(O)NH, NHC(O)NR$_B$, NR$_B$CO NR$_B$C(O)O, NR$_B$C(O)NH, NR$_B$C(O)NR$_B$, CS, C(S)O, C(S)NH, C(S)NR$_B$, OCS, OC(S)O, OC(S)NH, OC(S)NR$_B$, NHCS, NHC(S)O, NHC(S)NH, NHC(S)NR$_B$ NR$_B$CS NR$_B$C(S)O, NR$_B$C(S)NH, NR$_B$C(S)NR$_B$;

each R$_B$ is independently optionally substituted alkyl or optionally substituted aryl; and r is 3-20;

Z is a nanoparticle comprising a biologically active agent;

m is 1-1000 and n is 1-1000.

8. The composition of claim 7, wherein the nanoparticle has a diameter ranging from about 1 nm to about 500 nm.

9. The composition of claim 7, wherein the biologically active agent is selected from the group consisting of a nucleic acid, a polynucleotide, an amino acid, a peptide a protein, a polypeptide, a carbohydrate, a lipid, a glycoprotein, a glycan, a lipoprotein, and a small molecule.

10. The composition of claim 7, wherein the biologically active agent is selected from the group consisting of an anti-AIDS agent, anti-cancer agent, antibiotic, antioxidants, immunosuppressant, anti-viral agent, enzyme inhibitor, protease inhibitor, reverse transcriptase inhibitor, fusion inhibitor, neurotoxin, opiod, hypnotic, anti-histamine, lubricant, tranquilizer, anti-convulsant, muscle relaxant, anti-Parkinson agent, anti-spasmodic, muscle contractant, channel blocker, miotic, anti-cholinergic, anti-glaucoma agent, anti-parasite, anti-protozoal, modulator of cell-extracellular matrix interaction, cell growth inhibitor, anti-adhesion agent, vasodilating agent, inhibitor of DNA, inhibitor of RNA, inhibitor of protein synthesis, inhibitors of apoptotic genes, modulators of transcription factors, anti-hypertensive, analgesic, anti-pyretic, steroidal anti-inflammatory agent, non steroidal anti-inflammatory agent, anti-angiogenic, anti-secretory, anticoagulant, antithrombotic agent, local anesthetic, ophthalmic, prostaglandin, anti-depressant, anti-psychotic, anti-emetic, antiproliferative, antimigration, antiangiogenic, antithrombotic, anti-inflammatory, antiphlogistic, cytostatic, cytotoxic, anticoagulative, antibacterial, antiviral and/or antimycotic agent and an imaging agent.

11. The nanoparticle composition of claim 7, wherein the nanoparticles are capable of inhibiting the growth of prostate cancer cells.

12. The nanoparticle composition of claim 7, wherein the nanoparticles are capable of inhibiting the growth of prostate cancer cells.

13. A nanoparticle composition of formula I:

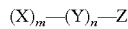

wherein
X is an organic small molecule PSMA inhibitor of formula III:

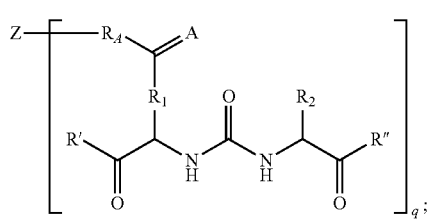

wherein,
R$_1$ is (CH$_2$)$_p$—NR$_3$—Y, wherein p is 1-6;
R$_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, or optionally substituted carbocyclic;
R' and R" are each independently —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O—R$_4$, —C(O)R$_4$, —C(O)NR$_3$R$_4$, or —N(R$_3$)C(O)R$_4$;
R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;
A is O, S, NH, N(alkyl) or N(aryl); and
R$_A$ is (CH$_2$)$_r$-Q-Z;
Q is CO, C(O)O, C(O)NH, C(O)NR$_B$, OCO, OC(O)O, OC(O)NH, OC(O)NR$_B$ NHCO NHC(O)O, NHC(O)NH, NHC(O)NR$_B$ NR$_B$CO NR$_B$C(O)O, NR$_B$C(O)NH, NR$_B$C(O)NR$_B$, CS, C(S)O, C(S)NH, C(S)NR$_B$, OCS, OC(S)O, OC(S)NH, OC(S)NR$_B$, NHCS, NHC(S)O, NHC(S)NH, NHC(S)NR$_B$, NR$_B$CS NR$_B$C(S)O, NR$_B$C(S)NH, NR$_B$C(S)NR$_B$;
each R$_B$ is independently optionally substituted alkyl or optionally substituted aryl; and
r is 3-20;
Y is

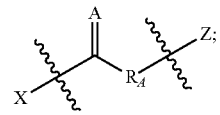

wherein
A is O, S, NH, N(alkyl) or N(aryl); and
Z is a nanoparticle comprising a biologically active agent; and
q is 1-1000;
or a pharmaceutically acceptable salt thereof.

14. A nanoparticle composition of formula I:

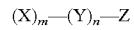

wherein
X is an organic small molecule PSMA inhibitor inhibitor of formula IV:

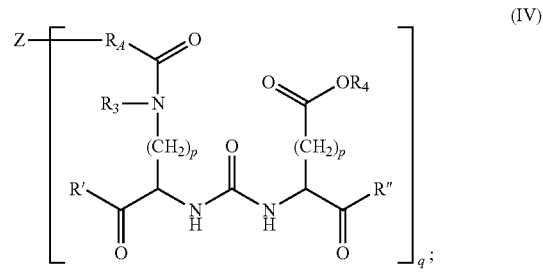

wherein,
p is independently 1-6;
R' and R" are each independently —OR$_4$, —SR$_4$, —SOR$_4$, —SO$_2$R$_4$, —N(R$_3$)S(O)$_2$—R$_4$, —N(R$_3$)(SO$_2$)NR$_3$R$_4$, —NR$_3$R$_4$, —C(O)—O—R$_4$, —C(O)R$_4$, —C(O)NR$_3$R$_4$, or —N(R$_3$)C(O)R$_4$;
R$_3$ and R$_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;
R$_A$ is (CH$_2$)$_r$-Q-Z;
Q is CO, C(O)O, C(O)NH, C(O)NR$_B$, OCO, OC(O)O, OC(O)NH, OC(O)NR$_B$ NHCO NHC(O)O, NHC(O)NH, NHC(O)NR$_B$, NR$_B$CO NR$_B$C(O)O, NR$_B$C(O)NH, $NR_BC(O)NR_B$, CS, C(S)O, C(S)NH, $C(S)NR_B$, OCS, OC(S)O, OC(S)NH, $OC(S)NR_B$, NHCS, NHC(S)O, NHC(S)NH, $NHC(S)NR_B$ $NR_BCS$ $NR_BC(S)O$, $NR_BC(S)NH$, $NR_BC(S)NR_B$;

each $R_B$ is independently optionally substituted alkyl or optionally substituted aryl; and r is 3-20;

Y is

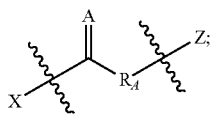

wherein

A is O, S, NH, N(alkyl) or N(aryl); and

Z is a nanoparticle comprising a biologically active agent; and q is 1-1000;

or a pharmaceutically acceptable salt thereof.

15. A nanoparticle composition comprising, a) a prostate specific membrane antigen (PSMA) inhibitor that is a compound of formula II,

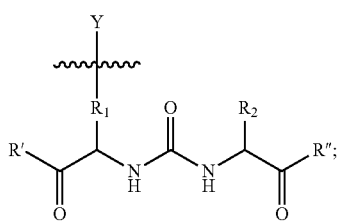

(II)

wherein, $R_1$ is $(CH_2)_p$—$NR_3$—Y, wherein p is 1-6;

$R_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, optionally substituted alkylcarboxy, or optionally substituted carbocyclic;

R' and R" are each independently —$OR_4$, —$SR_4$, —$SOR_4$, —$SO_2R_4$, —$N(R_3)S(O)_2$—$R_4$, —$N(R_3)(SO_2)NR_3R_4$, —$NR_3R_4$, —C(O)—O—$R_4$, —$C(O)R_4$, —$C(O)NR_3R_4$, or —$N(R_3)C(O)R_4$;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

Y is —(C=A)-$R_A$—, wherein A is O, and $R_A$ is

Q is CO, C(O)O, C(O)NH, $C(O)NR_B$, OCO, OC(O)O, OC(O)NH, $OC(O)NR_B$ NHCO NHC(O)O, NHC(O)NH, $NHC(O)NR_B$, $NR_BCO$ $NR_BC(O)O$, $NR_BC(O)NH$, $NR_BC(O)NR_B$, CS, C(S)O, C(S)NH, $C(S)NR_B$, OCS, OC(S)O, OC(S)NH, $OC(S)NR_B$, NHCS, NHC(S)O, NHC(S)NH, $NHC(S)NR_B$, $NR_BCS$ $NR_BC(S)O$, $NR_BC(S)NH$, $NR_BC(S)NR_B$;

each $R_B$ is independently optionally substituted alkyl or optionally substituted aryl; and r is 3-20;

or a pharmaceutically acceptable salt thereof;

wherein the prostate specific membrane antigen (PSMA) inhibitor is conjugated to an α-amino-ω-hydroxy terminated poly(ethylene glycol-b-ε-caprolactone) (PEG-PCL) polymer chain; and the PEG-PCL polymer chain is conjugated to a nanoparticle comprising a biologically active agent.

16. The nanoparticle composition of claim 15, wherein the biologically active agent is docetaxel.

17. The nanoparticle composition of claim 15, wherein the nanoparticles are capable of binding PSMA.

18. A method for treating a disease or disorder in a subject, the method comprising the step of administering to the subject a nanoparticle composition of claim 1, such that the administration of the nanoparticle composition is effective to treat said disease or disorder.

19. The method of claim 18, wherein the disease is cancer or a proliferation disease.

20. The method of claim 19, wherein the disease is cancer, tumor or carcinoma.

21. The method of claim 20, wherein the disease is prostate cancer, bladder cancer, bone cancer, brain cancer, breast cancer, cervical cancer, colon cancer, epithelial cancers, esophageal cancer, gastrointestinal cancers, gall bladder cancer, gynecological cancers, kidney cancer, laryngeal cancer, liver cancer, lung cancer, nose cancer, ovarian cancer, pancreatic cancer, rectum cancer, Schneeberg lung cancer, skin cancer, squamus cell and/or basal cell cancers, stomach cancer, testicular cancer, throat cancer, tongue cancer, urethral cancer, uterine cancer, vaginal cancer, cancer of the large intestine, cancer of the small intestine, cancer in the area of the mouth and on the lip, brain tumors (gliomas), connective tissue tumor, Ewing tumors, eye tumors, germ cell tumor, hypophysis tumor, osteolytic tumors and osteoblastic tumors, soft tissue tumors, urological tumors, Wilm's tumor, tumors of the small intestine, tumors of ear, nose and throat, head and neck tumors (tumors situated in the region of the neck, nose and ears), tumor of the eyelid, acute myeloid leukemia (AML), acute promyelocytic leukemia (APL), adenocarcinomas, acute leukemia, acoustic neurinoma, ampullary carcinoma, anal carcinoma, astrocytomas, basal cell carcinoma, brain metastases, breast carcinoma, bronchial carcinoma, Burkitt's lymphoma, Canine B-Cell Lymphoma, carcinoids, choroidal melanoma, chronic myelogenous leukemia (CML), colorectal carcinoma, colon carcinoma, craniopharyngiomas, corpus carcinoma, CUP syndrome, endometrial carcinoma, ependymoma, epithelial cell-derived neoplasia (epithelial carcinoma), esophageal carcinoma, gall carcinomas, glioblastomas, hairy cell leukemia, head and neck squamous cell carcinoma, hematological neoplasias, hepatocellular carcinoma, Hodgkin's disease, Kaposi's sarcoma, liver metastases, leukemia, lymphomas, malignant lymphoma (Hodgkin/Non-Hodgkin), malignant melanoma, malignant neoplasma, malignomas of the gastrointestinal tract, medulloblastomas, melanoma, meningiomas, mycosis fungoides, myelomas, neurinoma, neuroblastoma, Non-Hodgkin's lymphomas, non-small cell bronchial carcinoma, oligodendroglioma, osteosarcoma, ovarian carcinoma, pancreatic carcinoma, papillary renal carcinoma, penile carcinoma, plasmacytoma, prostate carcinoma, rectal carcinoma, renal cell carcinoma, retinoblastoma, squamous cell carcinoma of the head and the neck, soft tissue sarcoma, spinocellular carcinoma, T-cell lymphoma (Mycosis fungoides), thymoma, thyroid carcinoma, tube carcinoma, urothelial carcinoma, vulvar carcinoma, wart appearance, and solid tumors.

22. The method of claim 20, wherein the disease is cancer, wherein the cancer comprises a neovasculature expressing PSMA.

23. The method of claim 22, wherein the disease is prostate cancer, renal cell carcinoma, glioblastoma, colon cancer, gastric cancer, bladder cancer, pancreatic cancer, sarcoma, melanoma, skin cancer and lung cancer.

24. The method of claim 18, wherein the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, complications associated with hypertension and/or heart failure, vascular organ damage, restenosis, cardiomyopathy, stroke, ischemic stroke, hemorrhagic stroke, reperfusion injury, renal reperfusion injury, ischemia, brain ischemia, ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, pneumonia, herpes virus, myalgias due to infection, influenza, autoimmune disease, graft vs. host reaction and allograft rejections, treatment of bone resorption diseases, osteoporosis, multiple sclerosis, angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy.

25. The method of claim 18, wherein the subject is a human.

26. A method of synthesizing a compound of formula II in claim 7, comprising the steps of:

a) reacting a compound of formula A:

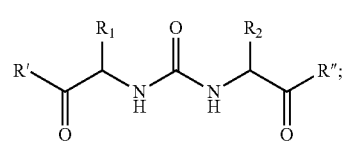

(A)

wherein, $R_1$ is $(CH_2)_p$—$NR_3$—Y, wherein p is 1-6;

$R_2$ is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

R' and R" are each independently —$OR_4$, —$SR_4$, —$SOR_4$, —$SO_2R_4$, —$N(R_3)S(O)_2$—$R_4$, —$N(R_3)(SO_2)NR_3R_4$, —$NR_3R_4$, —C(O)—O—$R_4$, —C(O)$R_4$, —C(O)$NR_3R_4$, or —$N(R_3)C(O)R_4$;

$R_3$ and $R_4$ are each independently selected at each occurrence from the following: H, optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; or optionally substituted carbocyclic;

with a compound of formula B:

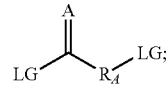

wherein

A is O, S, NH, N(alkyl) or N(aryl);

$R_A$ is $(CH_2)_r$-Q-Z;

Q is CO, C(O)O, C(O)NH, C(O)$NR_B$, OCO, OC(O)O, OC(O)NH, OC(O)$NR_B$, NHCO, NHC(O)O, NHC(O)NH, NHC(O)$NR_B$, $NR_B$CO $NR_B$C(O)O, $NR_B$C(O)NH, $NR_B$C(O)$NR_B$, CS, C(S)O, C(S)NH, C(S)$NR_B$, OCS, OC(S)O, OC(S)NH, OC(S)$NR_B$, NHCS, NHC(S)O, NHC(S)NH, NHC(S)$NR_B$ $NR_B$CS $NR_B$C(S)O, $NR_B$C(S)NH, $NR_B$C(S)$NR_B$;

each $R_B$ is independently optionally substituted alkyl or optionally substituted aryl; and r is 3-20; and each LG is independently a leaving group; and b) reacting the product of step a) with a nanoparticle comprising a biologically active agent to form a composition of formula II.

* * * * *